(12) United States Patent
van't Oever et al.

(10) Patent No.: US 6,630,990 B2
(45) Date of Patent: Oct. 7, 2003

(54) OPTICAL METHOD AND APPARATUS FOR RED BLOOD CELL DIFFERENTIATION ON A CELL-BY-CELL BASIS, AND SIMULTANEOUS ANALYSIS OF WHITE BLOOD CELL DIFFERENTIATION

(75) Inventors: Ronny van't Oever, Enschede (NL); Young Ran Kim, Sunnyvale, CA (US); James C. Bearden, Jr., Milpitas, CA (US); Marilou Z. Landayan, Newark, CA (US)

(73) Assignee: Abbott Laboratories, Abbott Park, IL (US)

( * ) Notice: Subject to any disclaimer, the term of this patent is extended or adjusted under 35 U.S.C. 154(b) by 2 days.

(21) Appl. No.: 09/874,493

(22) Filed: Jun. 5, 2001

(65) Prior Publication Data

US 2003/0025896 A1 Feb. 6, 2003

(51) Int. Cl.$^7$ ............................................... G01N 33/48
(52) U.S. Cl. ........................... 356/39; 356/40; 356/337; 356/441; 356/336; 356/339; 356/340
(58) Field of Search ............................. 356/39, 40, 337, 356/441, 336, 339, 340, 364; 436/63, 343, 72, 73

(56) References Cited

U.S. PATENT DOCUMENTS

| 4,586,190 A | * | 4/1986 | Tsuji ............................ 377/10 |
| 4,735,504 A | | 4/1988 | Tycko |
| 4,882,284 A | * | 11/1989 | Kirchanski et al. ........... 436/63 |
| 5,194,909 A | | 3/1993 | Tycko |
| 5,284,771 A | | 2/1994 | Fan et al. |
| 5,350,695 A | | 9/1994 | Colella et al. |
| 5,360,739 A | | 11/1994 | Fan et al. |
| 5,438,003 A | | 8/1995 | Colella et al. |
| 5,559,037 A | | 9/1996 | Kim et al. |
| 5,616,501 A | * | 4/1997 | Rodriguez et al. ............ 436/63 |
| 5,631,165 A | | 5/1997 | Chupp et al. |
| 5,656,499 A | | 8/1997 | Chupp et al. |
| 5,691,204 A | | 11/1997 | Kim et al. |
| 5,798,827 A | * | 8/1998 | Frank et al. .................. 356/39 |
| 6,067,157 A | * | 5/2000 | Altendorf .................... 356/337 |

FOREIGN PATENT DOCUMENTS

EP 0 545 314 A1 * 11/1992 .......... G01N/15/14

* cited by examiner

*Primary Examiner*—Karl D. Frech
*Assistant Examiner*—Daniel A. Hess
(74) *Attorney, Agent, or Firm*—Regina M. Anderson; Mimi C. Goller

(57) ABSTRACT

Methods and apparatus are disclosed for determining the volume, hemoglobin concentration, maturity and cell shape of mammalian red blood cells in a whole blood sample and simultaneously monitoring system standardization. Methods for distinguishing red blood cells from other cellular particles, prior to the red blood cell analysis are also disclosed. Red blood cells are passed through a beam of light in single file at a selected wavelength, obtaining an initial cytogram by means of the resultant magnitude of one light loss signal and one forward angle light scatter signal at a selected angular interval and a third side angle light scatter or two forward angle light scatter signals at a selected angular intervals and a third side-angle light scatter signal, projecting the cytogram, point by point, onto a pre-calibrated 3-dimensional surface containing grid lines of volume and hemoglobin concentration and determining accurate values of cell volume and hemoglobin concentration.

21 Claims, 16 Drawing Sheets

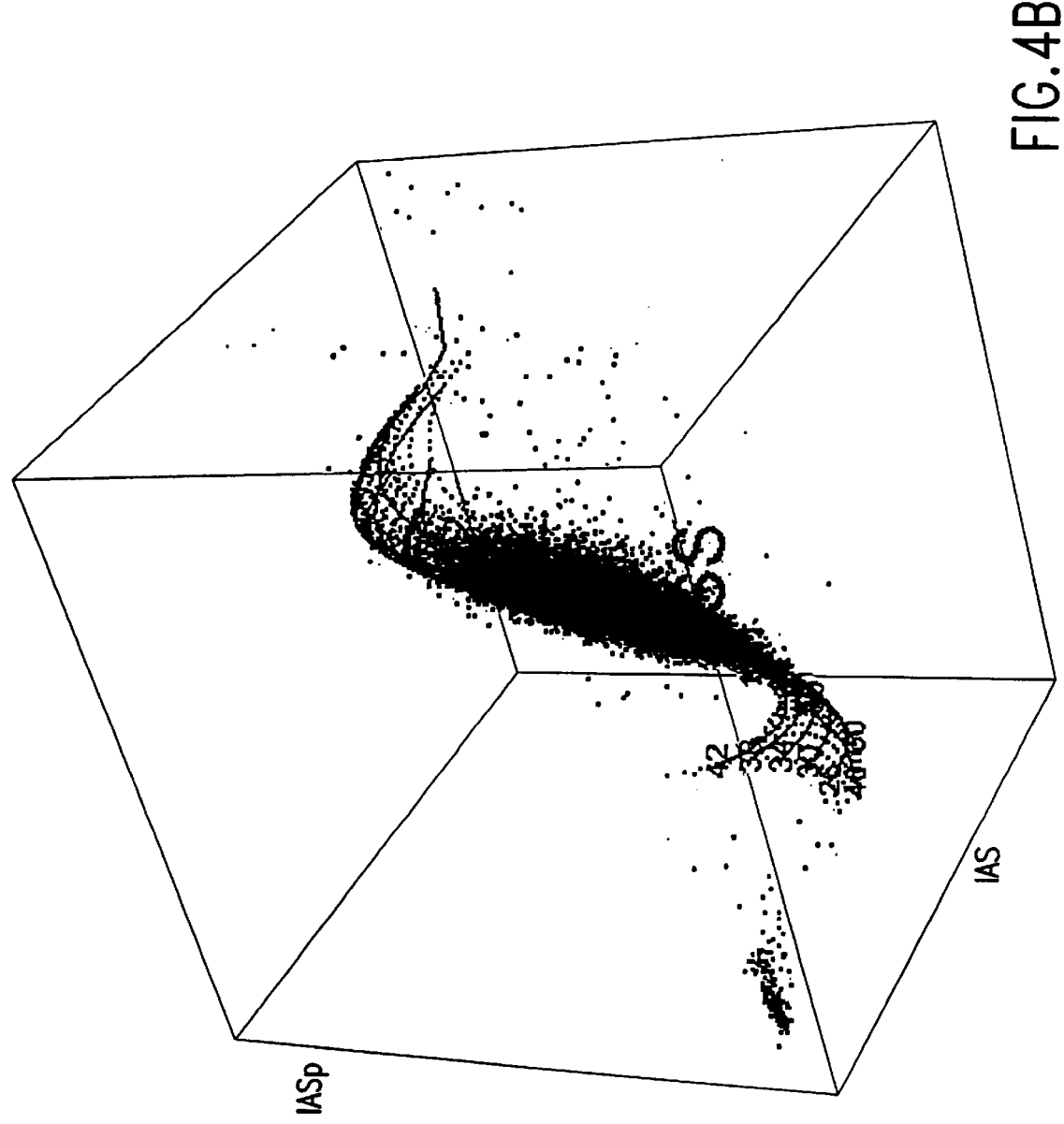

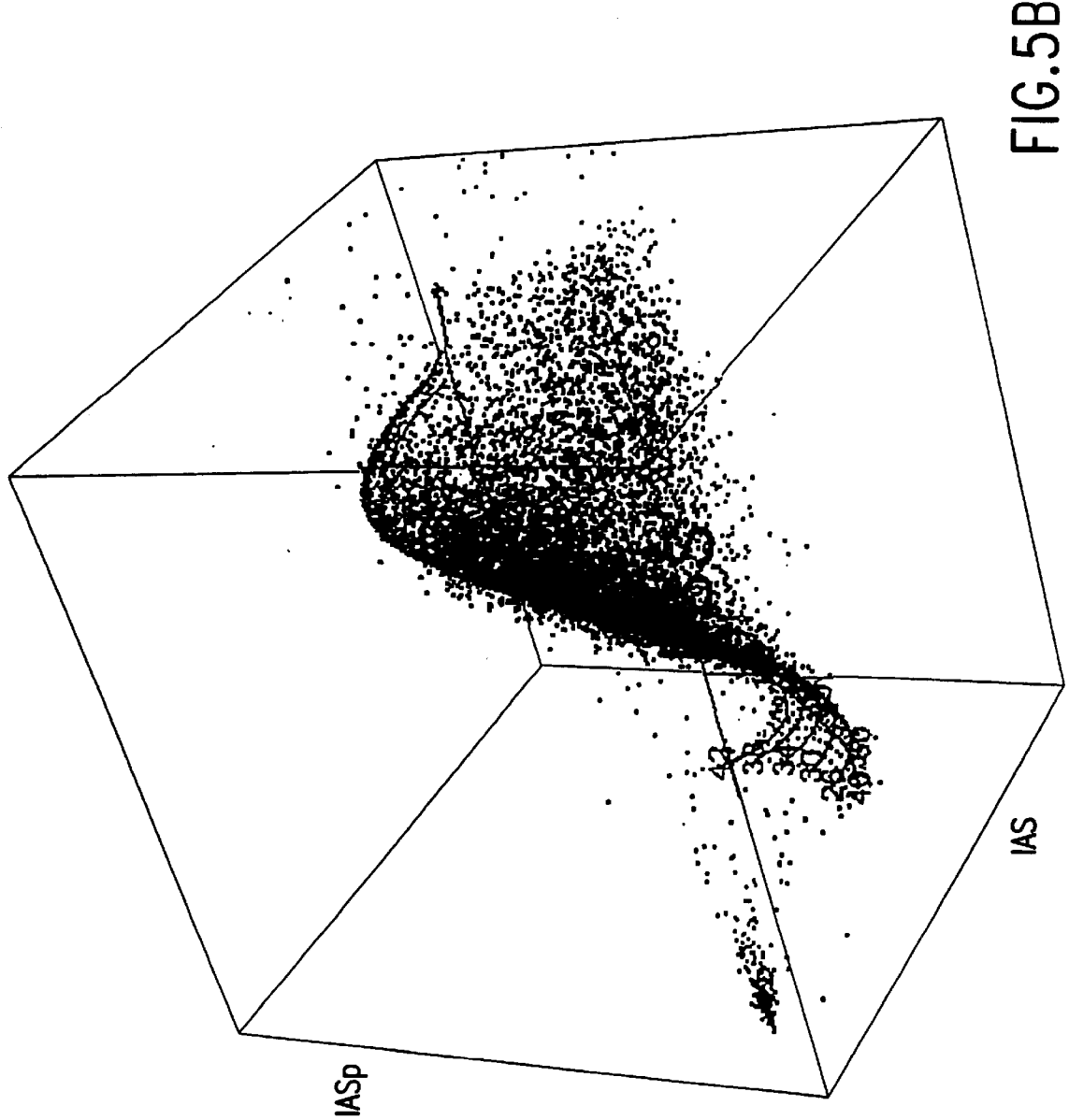

OPTICAL METHOD AND APPARATUS FOR RED BLOOD CELL DIFFERENTIATION ON A CELL-BY-CELL BASIS, AND SIMULTANEOUS ANALYSIS OF WHITE BLOOD CELL DIFFERENTIATION

SUMMARY OF INVENTION

Methods and apparatus are disclosed for determining the volume, hemoglobin concentration, maturity and cell shape of mammalian red blood cells in a sample and simultaneously monitoring system standardization. Methods for distinguishing red blood cells from other cellular particles, prior to the red blood cell analysis are also disclosed. The method can be applied with accuracy over a wide range of visible spectrum. A whole blood sample is treated with a reagent solution containing a nonionic surfactant in an isotonic buffered solution at neutral pH, the red blood cells are passed through a beam of light in single file at a selected wavelength, obtaining an initial cytogram by means of the resultant magnitude of one light loss signal and one forward angle light scatter signal at a selected angular interval and a third side angle light scatter or two forward angle light scatter signals at selected angular intervals and a third side-angle light scatter signal, projecting the cytogram, point by point, onto a pre-calibrated 3-dimensional surface containing grid lines of volume and hemoglobin concentration, determining accurate values of cell volume and hemoglobin concentration by means of the location of each projected intercept onto the three dimensional grid surface.

BACKGROUND OF THE INVENTION

1. Field of the Invention

The present invention relates to a method and apparatus for simultaneous monitoring of system standardization and automated analysis of mammalian red blood cell (RBC) and white blood cell (WBC) differentiation in a body fluid. The present invention particularly relates to a multi-angle light scatter and fluorescence apparatus such as multi-parameter hematology analyzer or flow cytometer that can perform both RBC and WBC differential analysis using the same optical detection system. The present invention more particularly relates to (i) a method for RBC analysis for volume, hemoglobin content, cell shape, and maturity in whole blood; (ii) an accurate method for determination of immature RBC (reticulocyte) volume and hemoglobin content; (iii) a RBC method that can continuously monitor the system standardization while a blood sample is being analyzed for RBC differentiation; and (iv) a method that can measure both mature RBC and reticulocyte volume and hemoglobin content, using one reagent and (v) an apparatus that can perform both WBC and RBC differential analysis using the same optical detection system.

2. Description of Prior Art

The conventional hematology method, microscopic examination of patient blood smears for RBC morphology for cell size, cell shape, color (for hemoglobin content) and inclusions provides a wealth of information leading towards the diagnosis and monitoring patient's clinical conditions. Quite misleading impressions can be drawn, however, from substandard blood films, besides the fact that this manual method is very subjective and time consuming. During the past three decades, a number of automated hematology analyzers have become available to handle heavy laboratory work loads and to reduce labor. Most of these instruments measure mean corpuscular volume (MCV) and mean corpuscular hemoglobin concentration (MCHC) of red blood cells either by electrical impedance measurement or by light scatter optical measurement in combination with a colorimetric hemoglobin measurement. Because of incompleteness or ambiguity of morphological information in cell analysis from these systems, 5 to 10 percent of samples in hematology laboratories routinely undergo smear review for cell morphology using the microscopic method. More advanced hematology analyzers in terms of RBC morphology analysis are the Technicon H*1 and the Bayer ADVIA. Both systems are designed to measure red cell volume and hemoglobin concentration simultaneously on cell-by-cell basis, according to the teachings of D. H. Tycko, described in U.S. Pat. No. 4,735,504.

U.S. Pat. No. 4.735,504 to D. H. Tycko describes Method and Apparatus for Determining the Volume and Index of Refraction of Particles. He discloses the method for measuring V and HC of is ovolumetrically-sphered RBCs by 2 selected angular interval forward light scattering signals, S1 and S2, to determine volume (V) and hemoglobin concentration (HC). Drawbacks of the method are: 1) the wavelength of the light source must be long enough (e.g., 633 nm) to avoid hemoglobin absorption from RBCs, which precludes the choice of a light source more suitable for multi-parameter blood cell analysis (e.g., a 488 nm light source); 2) the two-dimensional (2D) matrix does not provide any information on abnormal cell shape since the signals from such cells fall on a wrong location on the predetermined 2D matrix, thus generating incorrect clinical data on V & HC; 3) the 2D matrix does not provide any information regarding shifts in the system standardization, the phenomenon that can occur without any warning due to an instability in fluidics passage caused by clots in certain blood samples or instability in electronics of the system; 4) the 2D scatter method is not capable of identifying and clearly separating WBC's and nucleated red blood cells (NRBCs) from mature RBC's or stained reticulocytes. WBC's and NRBC's generate much more scatter than RBC's because of their nuclei and if they are not excluded cleanly from the RBC population before V and HC analysis, clinical results on MCV, hematocrit (Hct), MCHC and mean corpuscular hemoglobin (MCH) will be very misleading on elevated WBC or NRBC samples.

U.S. Pat. No. 5,194,909 to D. H. Tycko teaches Apparatus and Method for measuring V and HC of Red Blood Cells. The difference of this art from that of his previous teachings in U.S. Pat. No. 4,735,504 is that the 2D matrix is created using one forward light scattering signal (pre-selected) at a long wavelength (633 nm) and the second signal from a resistant pulse-sizing aperture. Drawbacks of the method are: 1) the method requires two independent sources of detection system, which creates unnecessary complications such as synchronization of the two signals from two different detection systems; 2) the wavelength of the light source must be long enough to avoid hemoglobin absorption from RBCs, which limits the choice of light source for multi-parameter blood cell analysis; 3) the 2D matrix does not provide any information on abnormally shaped RBCs, thus generating incorrect clinical information on V & HC; 4) the 2D matrix does not provide any information regarding shifts in the system standardization, the phenomenon that can occur without any warning due to instability in electronics or fluidics as explained above.

U.S. Pat. No. 5,284,771 to Fan et al. discloses Reagent Compositions and their use in sphering cells. The reagent composition includes a zwitterionic surfactant for sphering red blood cells to eliminate orientation noise and Ozxazine750 to stain reticulocytes. The light source of the optical detection system is a 633 nm HeNe laser, and the stained reticulocytes are identified by light scatter/absorption technology. Fluorescent measurement of retoculocytes was not demonstrated or claimed in this patent. The inventors of this disclosure did not make any claims on reticulocyte V & HC measurements, but they described the use of the aforenoted methods of Tycko to simultaneously measure the red cell volume and hemoglobin on a cell-by-cell basis using the TECHNICON H*1 SYSTEM. In the teachings of Fan et al., the reticulocyte staining procedure requires manual preparation, manual feeding, and over 2 min. of staining time. The inventors described that V & HC of both RBCs and reticulocytes are measured by the method of Tycko, although the reagents used for RBCs and reticulocytes are completely different in composition. The reagent used to construct Tycko's 2D matrix for RBCs for the TECHNICON H*1 spheres and fixes the RBCs as described in Tycko's disclosure, while the reagent used for the reticulocytes spheres RBCs in a buffer that does not contain any fixative. Besides, absorption by the blue dye used to stain reticulocytes interferes with the magnitude of the scatter signals in the measurement of V & HC of the stained cells. Aforementioned problems may lead to erroneous clinical data on reticulocyte V & HC measurements by the teachings of Fan et al. As mentioned above, Tycko's method for V & HC measurement requires a light source which emits monochromatic light in a region where hemoglobin is very transparent. This limits the availability of the light source ($\lambda_{max}$ must be >600 nm, such as a red HeNe laser). Another limitation is the choice of available dyes, since the same wavelength must be used for the absorption, or to excite the dye for fluorescent emission. Under this condition, the dye must be a blue dye with a strong absorption of red light. No claims were made on the Reticulocyte V&HC measurement in this patent.

U.S. Pat. No. 5,350,695 to Collela et al. discloses the same methods and reagents for characterizing reticulocytes as previously disclosed in U.S. Pat. No. 5,284,771, except that a method of adjusting the measured absorption signals for pseudo-absorption is added. According to the description in the first paragraph, column 12, of this disclosure, the major problem of the invention disclosed in U.S. Pat. No. 5,284,771 is the absorption signals of TECHNICON H*1 instrument being at the same level as the noise of the absorption preamplifier. Therefore, they had to develop a mathematical model to improve the signal-to-noise (S/N) ratio of the absorption signals from the stained reticulocytes. Even with the mathematical correction disclosed in this patent, generating satisfactory SIN ratio of absorption signals from the stained reticulocytes appears to be the major problem of this method. Besides, light absorption will also interfere with the magnitude of light scatter of the particle.

U.S. Pat. No. 5.360,739 to Fan et al. discloses the methods and reagents as disclosed in the four previous patents, except that the blue excitable fluorescent dye, acridine orange, is included. To practice the teachings of this method, it requires two light sources, one for the blue excitable fluorescent measurement (Argon/Ion laser) and another for cell volume and hemoglobin measurement (HeNe laser). A drawback of this invention is making the detection system unnecessarily complicated for synchronization and standardization and increases the instrument production cost significantly.

U.S. Pat. No. 5,438,003 to Collela et al. discloses the same reagent compositions disclosed in the 4 previous patents for use in the identification and characterization of reticulocytes in whole blood. All the claims of this invention are related to reagent composition and no claims are made on the method of V & HC measurement of reticulocytes. However, they have a new and lengthy explanation in the text how they are correcting "pseudo-absorption" and hemoglobin interference in the disclosed method in separating reticulocytes from mature RBCs by light scatter/absorption utilizing a HeNe (633 nm) light source. Consequently, the cytograms presented in U.S. Pat. No. 5,43 8,003 reveal reticulocyte signals poorly separated from that of mature RBCs. It will be very difficult to accurately measure V and HC of reticulocytes unless the population is well separated from mature RBCs by the disclosed light scatter/absorption method.

Furthermore, the examples in this disclosure reveal that the disclosed method requires two reagents which are completely different from the reagent used to construct the 2D map for V&HC measurements, in pH, osmolarity, sphering agent, and buffer. In addition, the H*1 RBC method has a very short incubation time, whereas the staining time for reticulocytes in the disclosed reagent is 2 min. (30 seconds vs. 120 seconds). The RBC sphering process is a very sensitive and reversible process, requiring precise timing to obtain consistently reproducible V & HC data based on the two selected light scatter signals. Collela et al. neither disclose any time study data on V & HC nor disclose any reticulocyte V & HC data in this patent.

Given these aspects of prior art, it is desirable to offer an improved method and apparatus for complete RBC differential analysis and more accurate reticulocyte count and V & HC measurement. It is an object of the present invention to provide an apparatus that can perform both WBC and RBC differential analysis using a single light source and optical detection system. It is another object of the present invention to provide more complete RBC differential analysis that includes clinically useful MCHC measurement on cell-by-cell bases and detection and quantitation of abnormal shape RBCs. It is yet another object of the present invention is to provide a single reticulocyte reagent that can be used for V&HC measurement of both mature RBCs and reticulocytes. Further object of the present invention is to provide a method that does not limit the choice of the light source within the very narrow region. Yet another object of the present invention is to provide an RBC/diff method for continuous monitoring of the system stability. These and further objects of the invention will become apparent to those of ordinary skill in the art from the following descriptions and figures.

SUMMARY OF THE INVENTION

The present invention relates to (1) a method and apparatus for simultaneous monitoring of system standardization and automated analysis of RBC differentiation on a multi-angle light scatter and fluorescent hematology analyzer or flow cytometer; (2) an apparatus that can perform both WBC and RBC differential analyses using the same light source and the same optical detection system; (3) more particularly relates to a method for RBC analysis for volume, hemoglobin content, cell shape and maturity in whole blood or body fluid; (4) an accurate method for determination of reticulocyte (immature RBC) V&HC, useful for diagnosis of iron deficiency anemia in children and hemodialysis patients; (5) an RBC method that can continuously monitor the system standardization while a blood sample is being analyzed, the feature eliminates the possibility of reporting the wrong clinical data, caused by system drifts. The above goals are achieved using a well-defined and pre-calibrated 3-dimensional (3D) surface as the built-in measuring device, which is created using both theoretical and actual data (events) generated by the multi-angle light scatter and/or light loss measurements. Each event of normal RBCs should therefore fall upon this infinitesimally thin 3D surface. If a majority of cell signatures fall below or above the surface, creating another layer, it is an indication that the subject channel is out of standardization, either due to electronic or fluidic shift. A multi-dimensional analysis of three or more light scatter and/or light loss signals provides a degree of internal consistency. Abnormally shaped RBCs are defined by the closest distance of each event from the surface, since all normal RBC signals (sphered in the CELL DYN 4000 Diluent-Sheath) fall in close proximity to the surface. Reticulocytes are defined by the fluorescent intensity of each event treated with a nucleic acid stain in the CELL DYN 4000 Reticulocyte Reagent. The cell V&HC are determined based on the location of each event on the 3D matrix created by ALL/IAS'/PSS or IAS/IAS'/PSS. To achieve the above goals, the CELL DYN 4000 detector was modified to create 3 zones; the central rectangular zone (Zone 1) for axial light loss (0 degree, ALL) and the current CELL DYN 4000 intermediate angle (Zone 2), which is 2.24°–7.45° (IAS), is divided into three sub-zones, where the central zone (Zone 3) is 4.5°–5.5° (IAS'). The modified detector will be referred to as a 3-Ring detector in this disclosure. The 3D surface is constructed using the 2 angles (ALL and IAS', or IAS and IAS') generated by the aforementioned 3-ring detector, and polarized 90° side scatter (PSS) signal. The 3D principle is applicable to optical detection systems with a broad range of light source wavelengths (e.g., 488 nm, 532 nm or 633 nm).

BRIEF DESCRIPTION OF THE DRAWINGS

For a more complete understanding of the present invention, and the advantages thereof, reference is now made to the following descriptions taken in conjunction with the accompanying, in which:

FIG. 4b displays the side view of the same normal blood shown in FIG. 4a above, exhibiting a very tight symmetrical distribution surrounding the 3D surface. On the perfectly standardized and calibrated system, about 50% of the signals fall above the surface and 50% below the surface as shown here. Symbols: O for sphered mature red blood cells, R for stained reticulocytes, X for unsphered abnormal shape red blood cells, W for white blood cells, P for platelets.

FIG. 5b exhibits the side view of the same sickle cell sample on the 3D surface. The scatter signals from the abnormally shaped sickle cells are falling off the 3D surface, thereby producing asymmetrical distribution and farther distance than normal RBCs from the 3D surface. Symbols: O for sphered mature red blood cells, R for stained reticulocytes, X for unsphered abnormal shape red blood cells, W for white blood cells, P for platelets.

DESCRIPTION OF THE PREFERRED EMBODIMENTS

A) Apparatus

Figure 1A:
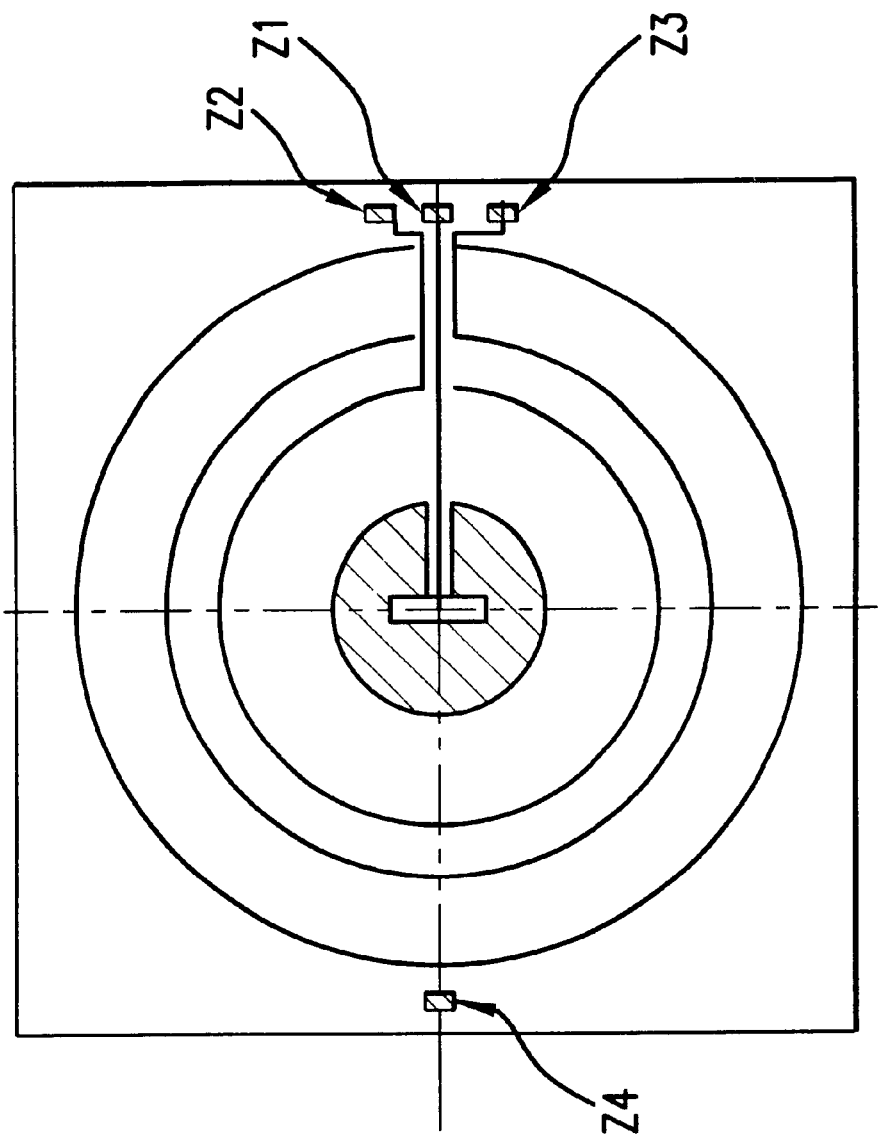
FIG. 1a is a pictorial presentation of the modified CELL DYN™ 4000 detector in order to use the same detector for both white blood cell differential (WBC/diff) and red blood cell differential (RBC/diff) analysis. Three (3) zones are created; the central rectangular zone (Zone 1:0° for ALL) for axial light loss; and the intermediate zone (Zone 2: 2.24–7.45° for IAS) is divided into three sub-zones, where the central zone (Zone 3) is 4.5–5.5 degrees (IAS').
Figure 1B:
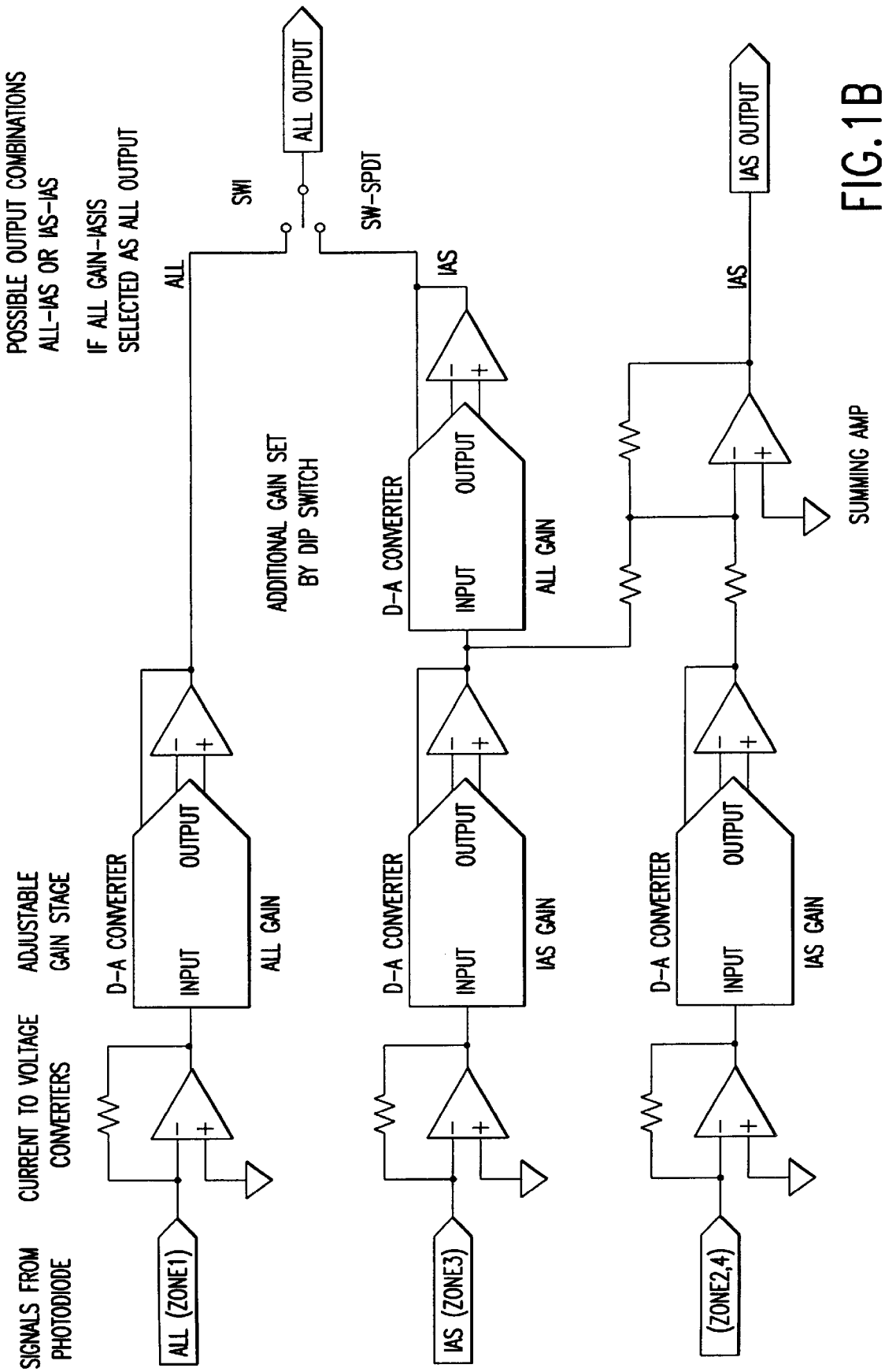
FIG. 1b describes the modification of the CELL DYN™ 4000 pre-amp board. The IAS output is created by electrically summing the signals from all 3 rings. The possible outputs from this modified pre-amp board are ALL and IAS or IAS' and IAS (or ALL and IAS' if rewired). The third angle used for both WBC/diff and the 3D RBC/diff analysis is 90° polarized side scatter.

One embodiment of the disclosed apparatus is a modified CELL DYN™ 4000 hematology analyzer disclosed in U.S. Pat. Nos. 5,656,499 and 5,631,165 entitled "METHOD AND APPARATUS FOR PERFORMING AUTOMATED ANALYSIS. To perform the disclosed method of the present invention, the CELL DYN™ 4000 system detector and the pre-amp board are modified. A pictorial presentation of the modified detector is presented in FIG. 1a: Three zones (3-Ring) are created; the central rectangular zone (Zone 1) for axial light loss (0 degree, ALL) and the intermediate zone (Zone 2, 2.24–7.45 degrees, IAS) is divided into 3 sub-zones, where the central zone (Zone 3) is 4.5–5.5 degrees (IAS'). The CELL DYN™ 4000 pre-amp board was also modified as illustrated in FIG. 1b. The modified pre-amp board creates the IAS output by electrically summing the signals from all 3 rings. The possible outputs from this modified pre-amp board are ALL and IAS or IAS' and IAS (or ALL and IAS' if rewired). If the gain of the ALL channel is set to 4, IAS' is then routed to the output instead of ALL. The IAS' gain is set by an on-board dual-in-line-package (DIP) switch. ALL and IAS are used for WBC/diff and either ALL and IAS' combination or IAS' and IAS combination is used for RBC/diff analysis. The third angle used for the 3D RBC/diff analysis is the side scatter signal which is constituted of a 125-degree cone. This is called polarized side scatter (PSS) as it essentially preserves the vertical polarization of the laser light. The same side collection system of 125-degree full angle cone also collects fluorescence signal of the reticulocytes stained by the RNA stain in the reagent disclosed in U.S. Pat. No. 5,691,204. This feature enables identification of reticulocytes as well as V&HC measurement of both mature RBCs and reticulocytes from a single reagent and a single light source, which is a unique feature of the present invention.

B) Methods & Reagents

WBC/diff Reagent: The composition of the CELL DYN™ 4000 WBC reagent used for WBC differential analysis and NRBC quantitation is disclosed in U.S. Pat. No.5,516,695 and the method of NRBC analysis is disclosed in U.S. Pat. No. 5,559,037.

RBC/diff Reagent: The composition of the CELL DYN™ 4000 Diluent-Sheath is disclosed in U.S. Pat. No. 5,656,499 and the CELL DYN™ 4000 Reticulcocyte reagent composition and the method is disclosed in U.S. Pat. No. 5,691, 204. Although both Diluent-Sheath and Reticulocyte Reagents are to perform the disclosed method on the CELL DYN™ 4000 system because of the pre-existing fluidics configuration on the system, the two reagents can be combined into one reagent to perform the disclosed method.

Methods: To perform the disclosed RBC differential analysis on the modified CELL DYN™ 4000, 36.1 µl of a whole blood sample is deposited by means of a sample aspiration probe into an RBC cup, which contains about 10,513 µl of the Diluent-Sheath, and mixed. The diluted sample is then transported to a sheathed impedance aperture to electronically determine the absolute RBC counts of the sample as described in U.S. Pat. Nos. 5,656,499 and No.5, 631,165 entitled "METHOD AND APPARATUS FOR PERFORMING AUTOMATED ANALYSIS". Then, about 450 µl of the diluted sample is transferred into the reticulocyte cup, which contains 450 µl of the reticulocyte reagent, where it is mixed and reticulocytes are stained. The prepared sample is then transported to the sheathed optical flow cell for detection. The cell stream passes through the flow cell, essentially one cell at a time, in a laminar-flowing, hydrodynamically-focused sample stream surrounded by the sheath. A beam of light, perpendicular to the flow axis, illuminates the stream. Light-scatter signals from a cell in the illuminated volume are detected by the disclosed 3-Ring detector (IAS and IAS'), and by two photomultiplier tubes (PMTs) which detect polarized side scatter (PSS) and green fluorescence (FL1). The amplitudes of these pulses are digitized and stored as list mode data. In the present embodiment, about 20,000 cells are counted in 8 seconds.

Figure 6A:
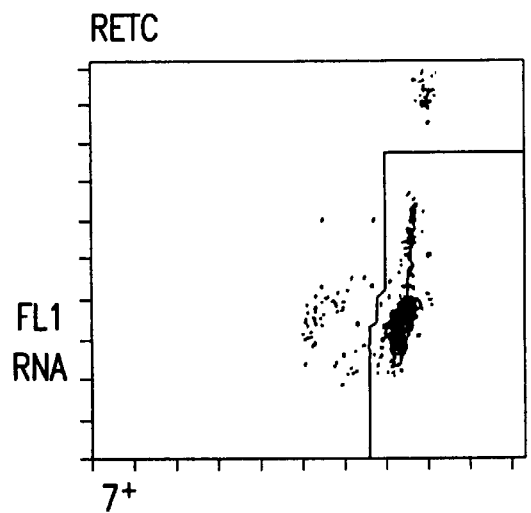
FIG. 6a displays the CELL DYN™ 4000 RBC/Retic cytogram (FL1 vs. IAS) of a high WBC sample. It reveals the clear separation and exclusion of WBC's from the RBC gate that includes stained reticulocytes and mature RBCs. The gated RBC population is used for reticulocyte count and V&HC measurements of both mature RBCs and reticulocytes.
Figure 6B:
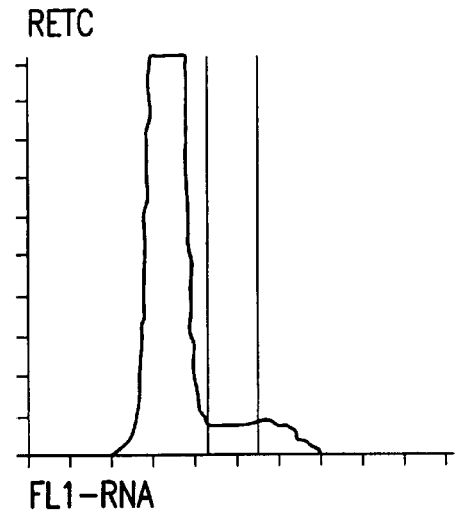
FIG. 6b is the FL1 histogram of the gated RBC population showing the regions for mature RBC's and for reticulocytes.

RBC Analysis: First, the signals which appear to the left of the RBCs in the FL1 vs. IAS cytogram shown in FIG. 6a are identified as platelets. The second step is to identify and label WBCs and NRBCs (if any), whose signals appear above the RBCs in the FL1 vs. IAS cytogram. The FL1 histogram (FIG. 6b) is scanned to determine the RBC gate's upper edge in the cytogram. The events within the gate are mature RBCs and reticulocytes.

Reticulocyte Detection: The method of the present invention has a high enough S/N ratio (stained reticulocytes vs. unstained mature RBCs) that no mathematical corrections are necessary to separate the signals. The FL1 histogram of the RBC population within the gate is scanned for a peak of mature RBCs, and then at higher FL1 values for either a valley between this peak and a second peak (a reticulocyte peak), or a decrease in slope (a reticulocyte "toe"), where a line is drawn to separate reticulocytes from mature RBCs, as described in the previous disclosure (U.S. Pat. No, 5,691, 204). Cells above this line are labeled as reticulocytes, the percent of reticulocytes (%R) is determined as a fraction of the total RBC population, and this %R is multiplied by the absolute concentration of RBCs in the sample, as determined from RBC impedance measurements, to get the absolute concentration of reticulocytes.

RBC/differential Analysis: The 3 scatter signals of the gated RBCs are analyzed and displayed on the standardized 3D surface. Details of the 3D surface construction is explained below:

System Gain Establishment for RBC/diff Analysis: Initially, a set of normal bloods with known reference values for MCV and MCHC are run in duplicate. The grand mean of MCV and MCHC of all readings are calculated. Then, the gains for each scatter channel (IAS, PSS, IAS' or ALL) are adjusted in such a way that the mean scatter signals of RBC population with MCV of 90 fL (normalized) and MCHC of 34 (normalized) will fall at channel 125 +/–3, the center of each scale (the Cell Dyn™ 4000 has a 256-channel linear scale for all scatter channels). Alternatively, stable beads with an appropriate refractive index, or stabilized human RBC's can be label-value-assigned with the mean of each scatter channel number on a standardized system, and used as standard particles.

Three (3)-Dimensional Surface Construction: As the first step, a theoretical model of the 3D map is constructed based on the Mie scattering theory. Minor adjustments are made to fit the scatter signals of RBC's with known MCV and MCHC perfectly to the surface (this is because some inaccuracies may have resulted due to the difficulty of accurately measuring the refractive index of hemoglobin solutions at 488 nm, due to absorption). The Mie scattering theory is based on the solution of the Maxwell equations for a normal illuminated homogenous sphere. The theory provides a calculation method of the intensities scattered by a sphere with a certain refractive index (Kerker, Bohren and Huffman). The theory requires the following input parameters:

a) Refractive Index of the sphere. This is a complex number when the sphere absorbs.
b) Refractive Index of the medium (the medium should not absorb light).
c) The wavelength and polarization of the light used for illumination.
d) The diameter of the sphere, which can be calculated from the volume.

One of the assumptions of the model is that the sphere is illuminated with a fixed intensity. This approximation is valid if the diameter of the beam illuminating the sphere is larger (approximately 10 times) than the diameter of the sphere. The basic assumption made for RBC's is that they are spheres and that they are homogeneous. This means that the refractive index of the cell is the same everywhere in the cell. The Mie scattering theory algorithm is based on the numerical solution of the Maxwell equations in a uniform electromagnetic field.

The Mietheory algorithm only gives the intensity distribution an angle theta. This is the angle between the direction of propagation of the beam and the direction of observation. This means that the scattered intensity profile is symmetric in the forward direction. The equation used to calculate the intensity collected by the different angles for incident linear polarized light is given by equation 1.

$$I(\theta, \varphi) = \frac{\lambda^2}{4\pi\gamma^2}(i_1 \sin^2\varphi + i_2 \cos^2\varphi) \quad \text{Equation 1}$$

Where:
$i_1 = |S_1(\theta)|^2$
$i_2 = |S_2(\theta)|^2$
I=intensity (relative number)
$\lambda$=wavelength (vacuum)
$\theta$=angle between laser direction and direction of observation
$\Phi$=angle between laser polarization and direction of observation
$i_1 i_2$=intensities for two different polarization directions The function Si ($\theta$) is calculated by the program The program gives the all the values of this function between 0° and 180° at angles separated by 0.3 degrees. At every angle, the value of this angle is obtained by the square of the absolute value. The angle $\Phi$ is the angle between the polarization vector and the direction of observation. In the CD4000, the polarization direction is the vertical axis. Thus, the function I($\theta$, $\Phi$) provides the intensity of the scattered light everywhere around the cell. To obtain the amount of light collected by the forward IAS detector, the intensity profile can be integrated over the collected angles. The numerical method for integration used in the program is the trapezium method. Because $\Phi$ is integrated over $2\pi$, the equation for scattering in the forward angles becomes:

$$\text{Forward Angle } (\theta_{min}, \theta_{max}) = \frac{\lambda^2}{4\pi} \int_{\theta_{min}}^{\theta_{max}} I_1(\theta) \sin\theta d\theta \quad \text{Equation 2}$$

The signal from the ALL detector equals the maximum intensity drop when a cell passes the laser beam. The ALL signal is the total light loss. This is also called the scatter extinction coefficient, which can be calculated by the algorithm developed by Bohren and Huffman.

The calculation of the PSS signal is straightforward, except that the detector collects a different vertical angle phi for every horizontal angle theta. For every horizontal angle $\Phi$, the integration for the vertical angle $\phi$ must be done. This integration is exact, so that no approximations have to be made. Every angle $\theta$ has its own minimum and maximum $\phi$, related to the shape of the cone, which is a circle in the case of the Cell Dyn™ 4000. The solution for the integration of $\sin^2(\Phi)$ is given in the equation 3.

$$\int_{-\varphi max}^{\varphi max} \sin^2(\varphi) d\varphi = \varphi_{max} - \text{Sin}(2\varphi_{max}) \quad \text{Equation 3}$$

The angles $\phi$ in this equation are given in radials and are $\frac{1}{4}*\pi$ smaller than the angles $\phi$ in the formula above. This is because phi is 90° plus and minus $\phi_{max}$ which is the vertical collection angle. The solution for $\cos^2(\phi)$ is similar, only the sign of the second term is different. For every angle $\theta$, the intensity collected in the vertical direction can be calculated. After integrating over the horizontal minimum and maximum angles$\theta$, the value for PSS is obtained.

Figure 2B:
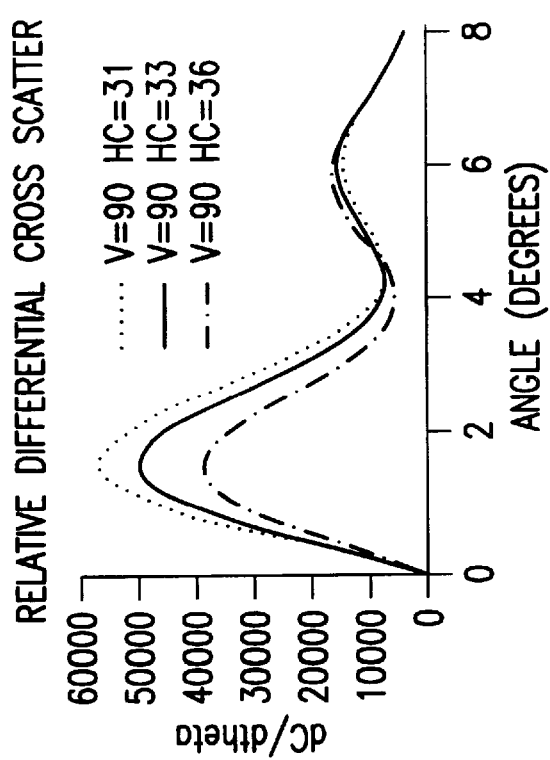
FIGS. 2a and 2b illustrate differential cross scatter in the forward angles for different values of volume and hemoglobin concentration at a wavelength of 488 nm.
Figure 2A:
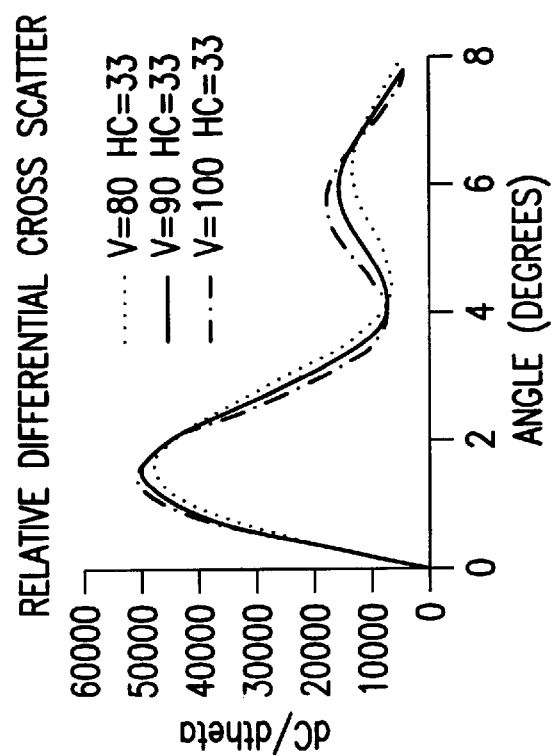

Selection of Forward Scatter Angles: The Cell Dyn™ 4000 forward scatter angle detector (IAS 3°–10° in air) is insensitive to volume. The theory requires that the collection angles must be defined in the suspension medium. The refractive index of the medium (CELL DYN™ 4000 Diluent-Sheath) at $\lambda_{max}^{25°\,C.}$ 488 nm is 1.339. Thus, according to Snell's law, the collection angle in the diluent is 2.24–7.45. FIGS. 2a and 2b display the relative differential cross scatter vs the angle in the diluent. The differential cross scatter is nothing less than the part below the integral in Equation 2.

The area below the curves represents the relative intensity for volume (V) and hemoglobin concentration (HC). The area below the curves for different V at a HC of 33 (g/dL) does not change very much between 2.24° and 7.45°, because the curve goes down with higher volume below 4 degrees and the curve goes up with volume above 4°. To be able to measure volume with minimal hemoglobin interference, the angles between 4.5° and 5.5° are selected. See FIGS. 2a and 2b above.

The measurements on different angles are achieved using the modified 3-Ring-detector. The detector is designed to have one inner ring covering the angles from 2.24° –4.5° and a second ring covering the angles from 4.5°–5.5° (IAS'), and a third ring that covers the angles 5.5°–7.45°. The three rings together will still give the angles collected by the current Cell Dyn™ 4000 IAS detector used for WBC differential analysis. It is possible to collect signals from the second ring only, which will be between 4.5 and 5.5. It is also possible to use the old and new angles at the same time. This approach has an advantage over prior art where two separate optical detection systems are used for WBC/diff and RBC/diff analysis. The present invention allows the use of the same optical detection system for both the WBC/diff and RBC/diff analyses at the same time. This approach creates various possibilities of collecting scattered light at different sets of angles.

Figure 3:
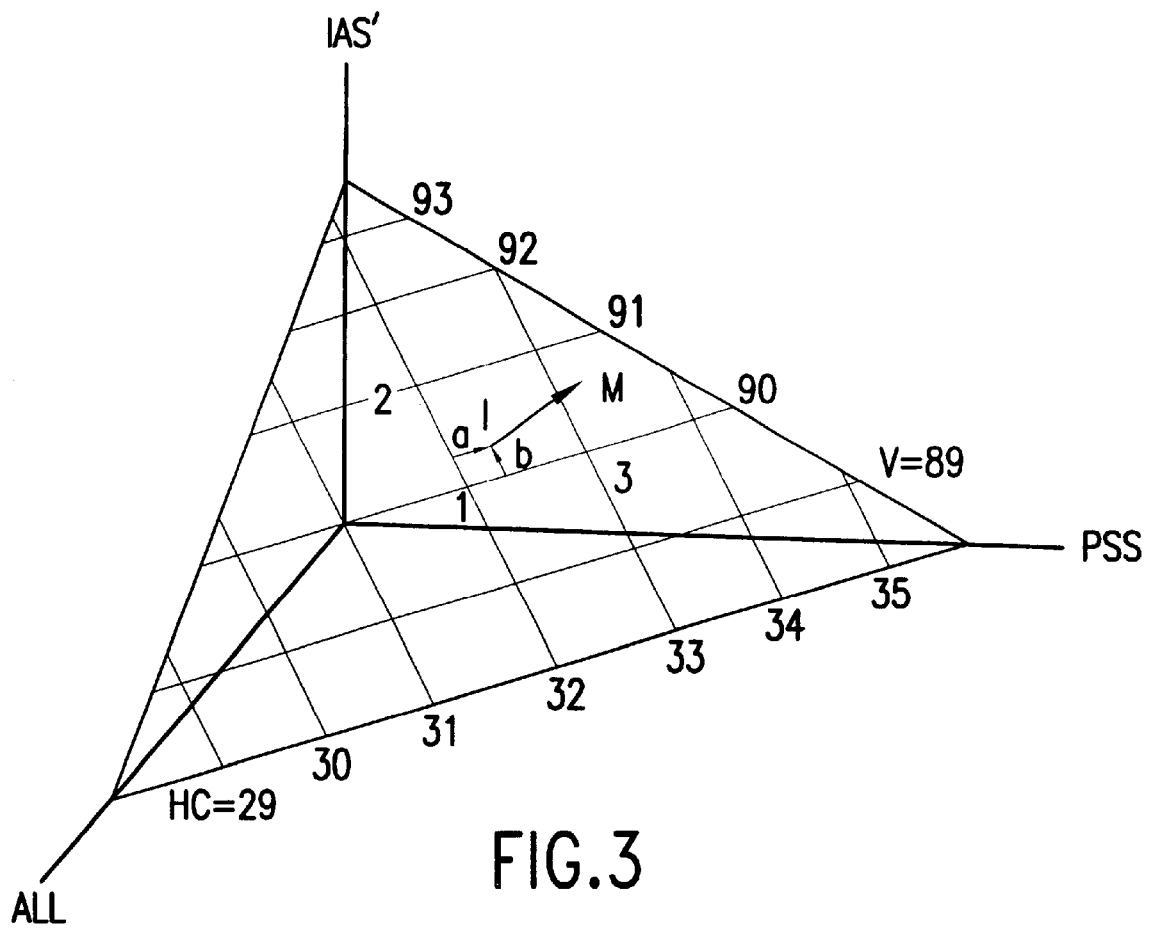
FIG. 3 is an example of a small portion of the aforementioned 3D surface to explain the principle how V&HC data of a cell is obtained from the 3D surface.

Three-dimensional (3D) cell analysis: Assuming that RBCs are perfectly sphered, the three scatter signals, IAS, IAS', and PSS (or ALL, IAS' and PSS) depend primarily on two RBC parameters, V and HC. All the possible V and HC combinations together create a surface in space. A simplified version of the surface in IAS', ALL and PSS in space is shown in FIG. 3. Only a small portion of the surface in 3D is displayed to explain the principle how the V and HC of a single cell is obtained. Assume that the surface is plane, although the surface is curved, in reality. But the same principle can be applied on the surface to find V and HC of a single RBC. When the system is perfectly standardized, all the sphered RBC's will be distributed very closely around the surface. Abnormally shaped-RBC's, such as sickle cells, will generate signals which are more distant from the surface. Thus, the distance from the surface of the RBC signals can be used in identifying abnormal cell shape.

The method of finding the V and HC information of a cell which is not exactly on the surface is explained below, using the cell M in FIG. 3. The point on the surface that is most likely to represent the V and HC of this cell is the closest point on the surface. In reality, there is not a real surface, but the locus of a set of known points with given V and HC values in 3D. The intercepts of the iso-V and iso-HC lines in FIG. 3 represent these points. To obtain the V and HC values of a point that is not exactly on this surface, the 3 closest points on this surface are found. In this case, the 3 closest points are 1, 2 and 3. The vector from 1 to 2 and the vector from 1 to 3 define a small part of the surface on which the normal can be calculated. Calculating the intercept with the surface of the vector parallel to the normal through point M, the point I is found. Point I represents the projection of the cell on the surface. If the intercept is found, the vector a and b can be calculated. The lengths of a and b can be used to interpolate between the values of the 3 points to get the V and HC of the cell (point M). By constructing a histogram of all cells of the distance in only the IAS direction to the surface, it is possible to see whether the surface is in the right place for the IAS signal. If the surface is set correctly for the IAS signals, the peak of the histogram will be at channel zero. This means that the same number of cells are on both sides of the surface. The same is true with ALL and PSS signals. As shown below, the 3 histograms for the distance to the surface in the 3 signal directions turned out to be a helpful tool for finding the right surface.

Finding the 3-D Surface: The Mie scattering theory predicts signals from a perfect sphere with a known refractive index. By calculating the signals for a range of refractive indices and V, the points on the surface can be found. The Mie theory provides only relative numbers of the signal intensities. Thus, the exact channel numbers of the 3 dimensions of the signal must be calculated by multiplying the gain factors to accurately place them on the surface. To be able to find these factors, three different hydrocarbons (heptane, nonane and dodecane) whose refractive indices fall within the clinical range of human red cell MCHC were used. Each of the 3 hydrocarbons, when mixed vigorously in the suspending medium, generate various size droplets with the same refractive index. Each of these 3 oils produces a well-defined V-signal distribution track, distinct from one another because of the difference in their refractive indices (the hydrocarbons have no absorption). Next, the accuracy of the surface constructed by the Mie theory is checked by measuring the distance of the actual signals to the closest point on the surface. For example, if the surface fits perfectly to the signals generated by the 3 hydrocarbons, the distance to the surface of the peak of the 3 histograms will be at zero.

Building a surface for blood sample is more complex because of light absorption by hemoglobin at 488 nm. To correct for absorption, the absorbance must be added to the as simulations used to create the 3D surface for the hydrocarbons. All the gain settings used for the 3 hydrocarbons to convert the theoretical values to channel numbers are kept constant. This way, a perfect surface that defines all possible RBC events is created. RBC's of a normal sample should be normally distributed around the surface. This surface also provides a tool to monitor system standardization while samples are being analyzed, without added effort for daily QC check for calibration and standardization of the instrument. For every sample, the 3D histograms of RBC's around the surface will be constructed during the signal processing. If the normal RBC distribution around the surface is not symmetrical, the instrument has gone out of standardization (e.g., fluidics or electronic problems).

For the sake of illustration, a number of uses of an preferred embodiment discussed herein are presented. The following discussion is provided for exemplary purposes only, and this discussion is not exhaustive. Specifically discussed below are ways of using a disclosed embodiment to perform an integrated blood cell analysis, an RBC differential analysis for volume, hemoglobin content, normal and abnormal cell shape, reticulocyte volume and hemoglobin content, on a multi-angle light-scatter and fluorescence hematology analyzer, using the same optical detection system used for WBC differential analysis, and to simultaneously monitor system standardization. This does not limit in anyway the scope of the claimed invention.

EXAMPLE 1

The disclosed apparatus is a modified CELL DYN™ 4000 (CD4000) system.

The CD4000 detector and Pre-amp board are modified in order to use the same detector for both white blood cell differential (WBC/diff) and red blood cell differential (RBC/diff) analyses. A pictorial presentation of the modified detector is seen in FIG. 1a: 3 zone are created; the central rectangular zone (Zone 1) for axial light loss (0 degree, ALL); the to intermediate zone (Zone 2, 2.24–7.45 degrees, IAS) is divided into three sub-zones, where the central zone (Zone 3) is 4.5–5.5 degrees (IAS'). The pre-amp board was modified as depicted in FIG. 1b. The modified pre-amp board creates the IAS output by electrically summing the signals from all 3 rings. The possible outputs from this modified pre-amp board are ALL and IAS, or IAS' and IAS (or ALL and IAS', if rewired). The IAS' gain is set by an on-board dual-in-line-package (DIP) switch. ALL and IAS are used for WBC/diff and either the ALL and IAS' or the IAS' and IAS combination, is used for RBC/diff analysis. The third angle used for 3D RBC/diff analysis is 90° polarized side scatter.

EXAMPLE 2

Figure 4A:
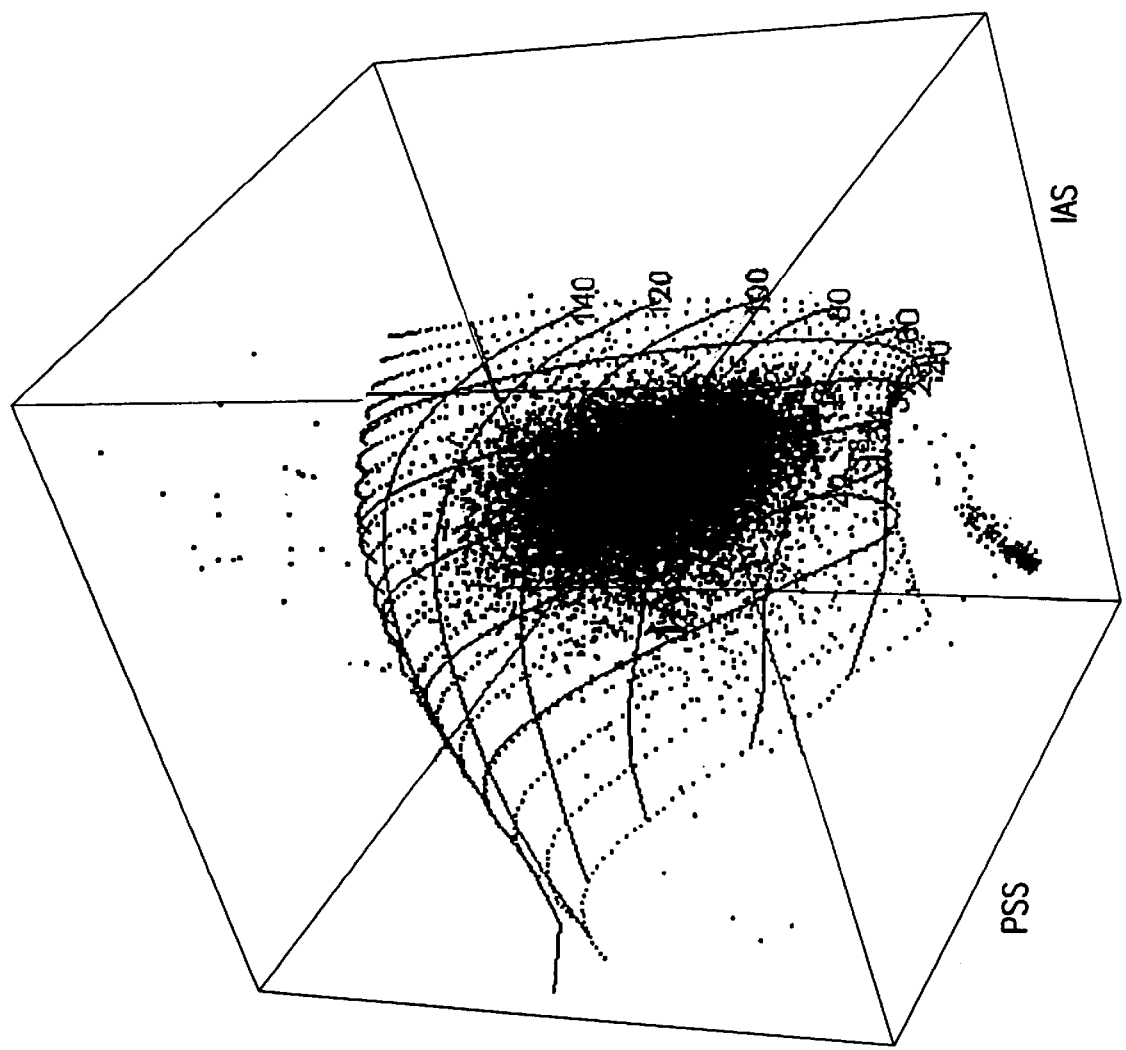
FIG. 4a exhibits the front view of a normal blood on the disclosed 3D surface. The CELL DYN™ 4000 system disclosed in U.S. Pat. Nos. 5,656,499 and 5,631,165 was modified with the disclosed 3-Ring detector and the pre-amp board as described in Example 1 and used to collect the presented data.

For this experiment, the CD4000 system described U.S. Pat. Nos. 5,656,499 and 5,631,165 entitled "METHOD AND APPARATUS FOR PERFORMING AUTOMATED ANALYSIS" was modified with the 3-Ring detector and the new pre-amp board as described in Example 1. About 112.5 $\mu$l of a normal whole blood sample is deposited by means of the sample aspiration probe into the RBC cup, which contains about 10,513 $\mu$l of the CD4000 Diluent-Sheath, and mixed. The diluted sample is then transported to a sheathed impedance aperture to electronically determine the absolute RBC counts, as described in U.S. Pat. Nos. 5,656,499 and 5,631,165. About 450 μl of the diluted sample is transferred into the CD4000 reticulocyte cup, which contains about 450 μl of the reticulocyte reagent (U.S. Pat. No. 5,691,204. Nov. 25, 1997. Compositions and methods for the rapid analysis of reticulocytes) and mixed. The prepared sample is then transported to the sheathed optical flow cell for detection. WBC's and NRBC's are eliminated by the RBC gate, and reticulocytes are identified and quantitated as described in U.S. Pat. Nos. 5,656,499 and 5,631,165). At the same time, the 3 scatter signals are also measured for each event and displayed on the standardized 3D surface. FIG. 4a and FIG. 4b exhibit the front view and the side view of a normal blood tightly over lapping on the 3D surface. On the perfectly standardized and calibrated system, about 50% of the signals fall above the surface, and 50% below the surface, as shown in FIG. 4b.

EXAMPLE 3

Figure 5A:
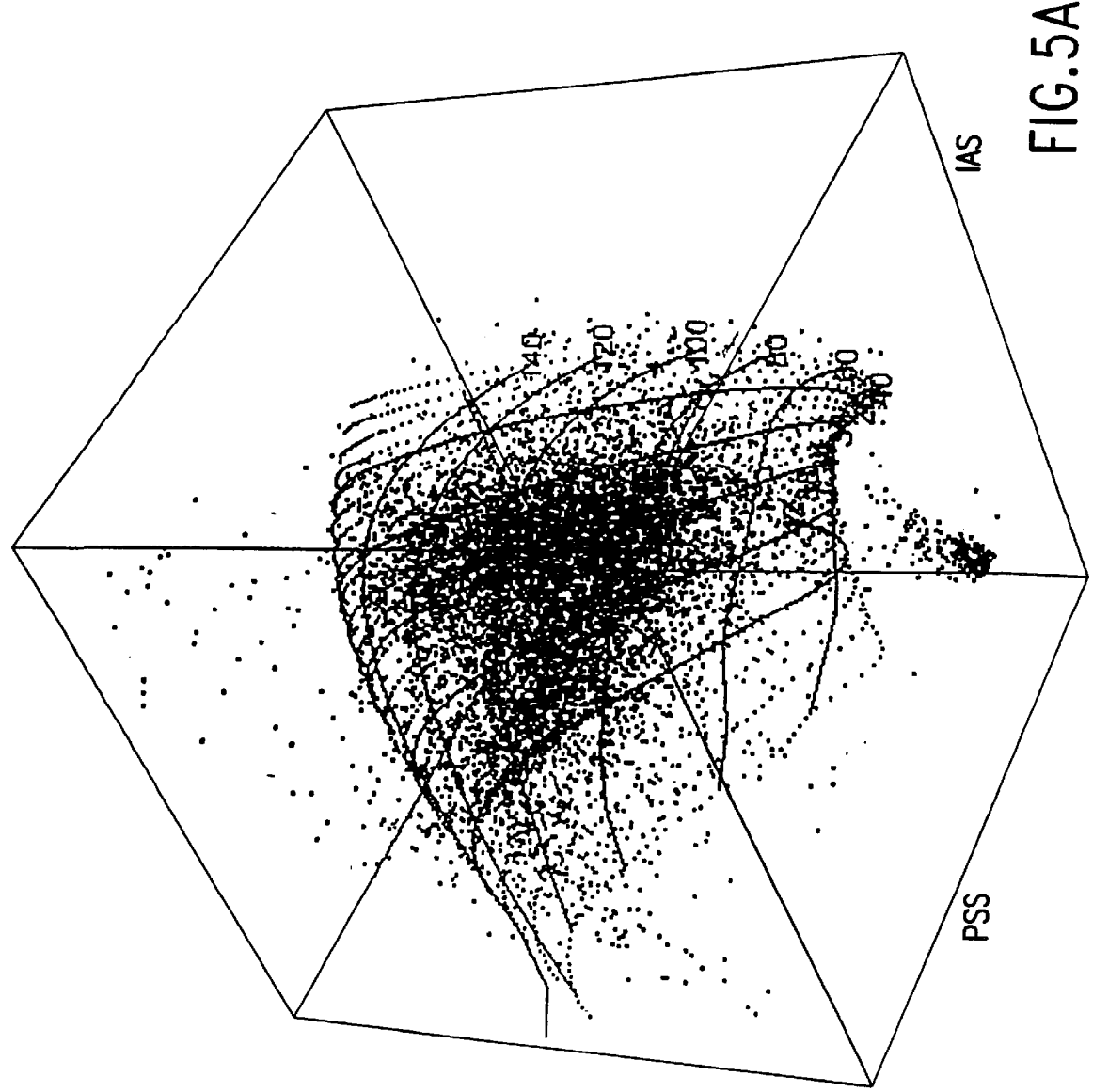
FIG. 5a presents the front view of a sickle cell sample on the same 3D surface shown in FIG. 4a. As shown, the cell population is much more dispersed due to abnormally shaped sickle cells.
Figure 5C:
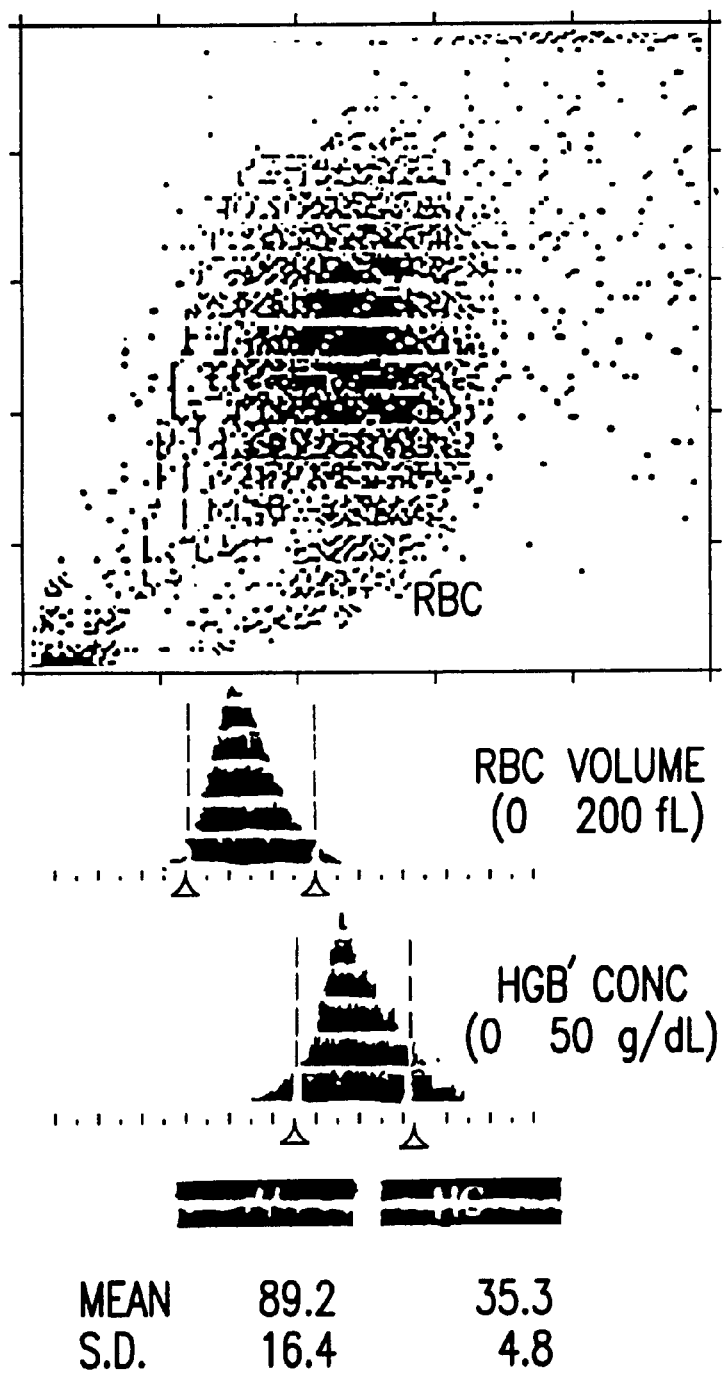
FIG. 5c is a 2D distribution of the same sample by prior art disclosed by Tycko (Bayer H*1).

A clinical blood sample containing sickle cells was run on the disclosed apparatus described in Example 2. FIG. 5a and FIG. 5b display the front and the side view of the sample, respectively. As can be seen, the cell population is much more dispersed, due to abnormally-shaped sickle cells, and the side view shows the signals falling off the 3D surface. Based on the distance from the surface of each event, the method of the present invention is capable of estimating the percent of abnormally shaped RBC's. The 2D distribution of prior art by Tycko (Bayer H*1) of the same sample is displayed in FIG. 5c. As can be seen in FIG. 5c, the 2D distribution does not distinguish abnormal cell shapes from sphered normocytes. Besides, a significant number of RBC's with abnormal shape fell off the 2D map, thereby excluded from the volume measurement.

EXAMPLE 4

Figure 6C:
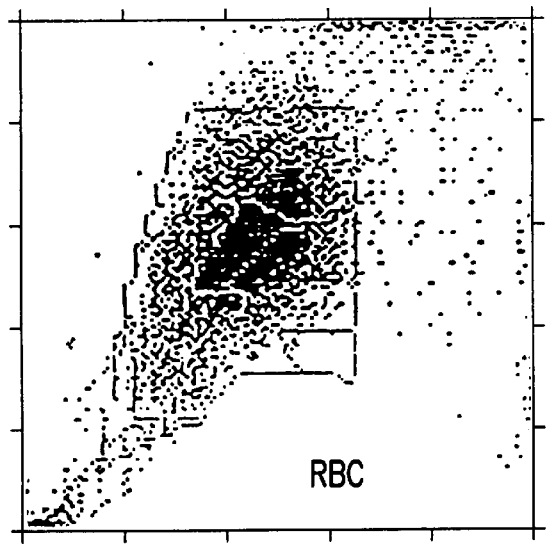
FIG. 6c is the 2D distribution of the same sample analyzed by prior art disclosed by Tycko. WBC's are not clearly separated from RBC's.

The CD4000 cytogram (FL1 vs. IAS) of a high WBC sample and the separation and exclusion of WBC's from the RBC gate, which includes stained reticulocytes and mature RBCs, is shown in FIG. 6a. As shown in FIG. 4a, the method of the present invention clearly identifies and eliminates WBC's from the RBC population before the RBC/diff analysis. FL1 histogram of the gated population is presented in FIG. 6b. On the contrary, the prior art disclosed by Tycko (Bayer H*1) does not clearly distinguish or separate WBC's from the RBC population (see FIG. 6c, RBC distribution of the same sample, by prior art). Therefore, the method of prior art may generate erroneous red cell MCV and MCHC results on elevated WBC samples from patients with various leukemias, especially chronic lymphocytic leukemia (CLL) since CLL lymphocytes are not only as small as RBC's but also fragile generating light scatter signals as small as RBC's.

EXAMPLE 5

Figure 7A:
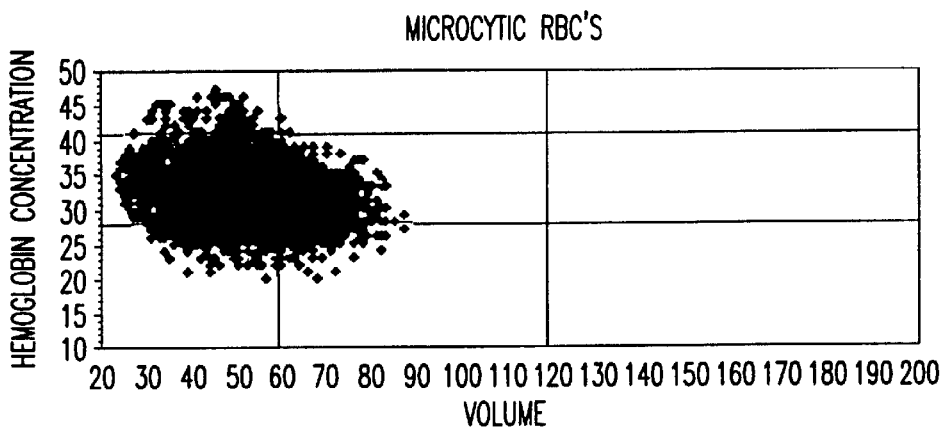
FIG. 7a displays a bivariate distribution of V&HC of a microcytic RBC sample.
Figure 7B:
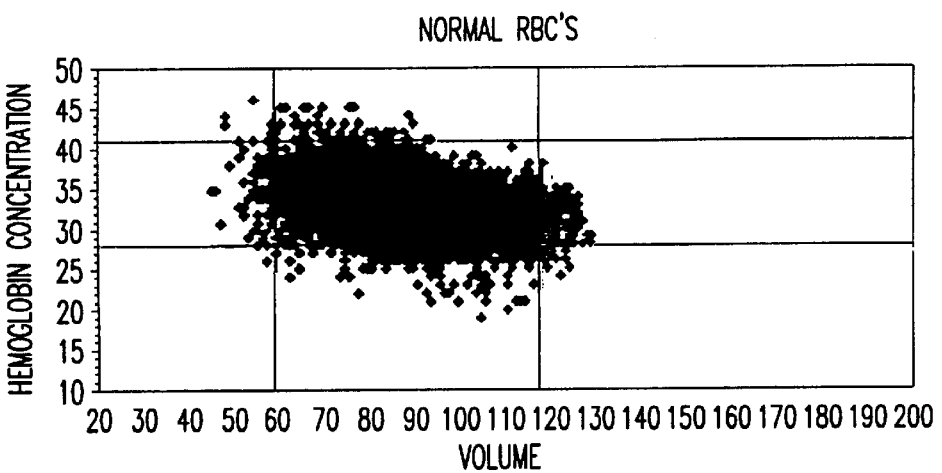
FIG. 7b shows a bivariate distribution of V&HC of a normal RBC sample.
Figure 7C:
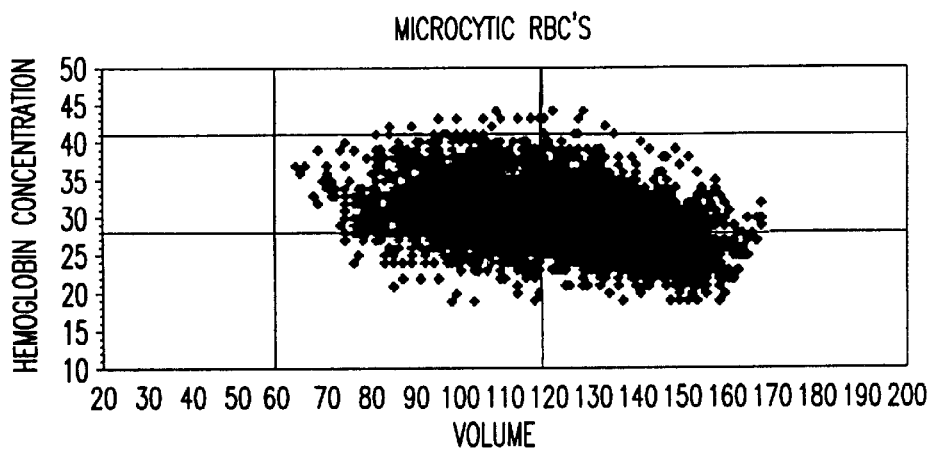
FIG. 7c displays a bivariate distribution of V&HC a macrocytic RBC sample.

Bivariate distribution of cell hemoglobin content (HC) vs. volume (V) of a microcytic (FIG. 7a), normocytic (FIG. 7b) and macrocytic (FIG. 7c) RBC samples, analyzed by the method of the present invention. Two fixed lines are drawn vertically and horizontally around the normal range, to identify and count different combinations of RBC abnormalities in size and hemoglobin content on each sample. The below Tables 1a, 1b, and 1c show the estimated percentages of cells in each category. Based on the information provided, the severity levels of anisocytosis, microcytosis, macrocytosis, hypochromia, and hyperchromia of the patient's condition can be determined.

TABLE 1a

Microcytic RBC Sample

|  | HC < 28 | 28 < = HC < = 41 | HC > 41 |
|---|---|---|---|
| V > 120 | 0.00% | 0.00% | 0.00% |
| 60 < = V < = 120 | 1.27% | 15.21% | 0.00% |
| V < 60 | 2.66% | 80.45% | 0.42% |

TABLE 1b

Normocytic RBC Sample

|  | HC < 28 | 28 < = HC < = 41 | HC > 41 |
|---|---|---|---|
| V > 120 | 0.04% | 0.59% | 0.00% |
| 60 < = V < = 120 | 2.04% | 96.34% | 0.31% |
| V < 60 | 0.02% | 0.62% | 0.05% |

TABLE 1c

Macrocytic RBC Sample

|  | HC < 28 | 28 < = HC < = 41 | HC > 41 |
|---|---|---|---|
| V > 120 | 14.32% | 41.35% | 0.05% |
| 60 < = V < = 120 | 4.48% | 39.67% | 0.13% |
| V < 60 | 0.00% | 0.00% | 0.00% |

EXAMPLE 6

Figure 8A:
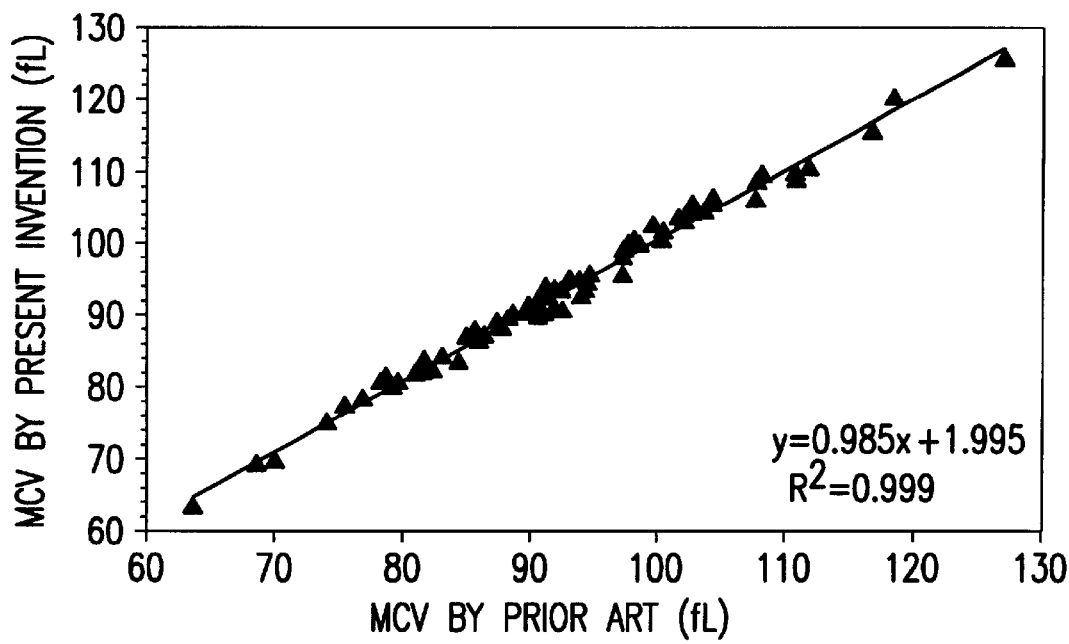
FIG. 8a shows the regression plot of mean corpuscular volume (MCV) results of the present invention vs. prior art by Tycko (Bayer H*1) on a set of normal and clinical samples.
Figure 8B:
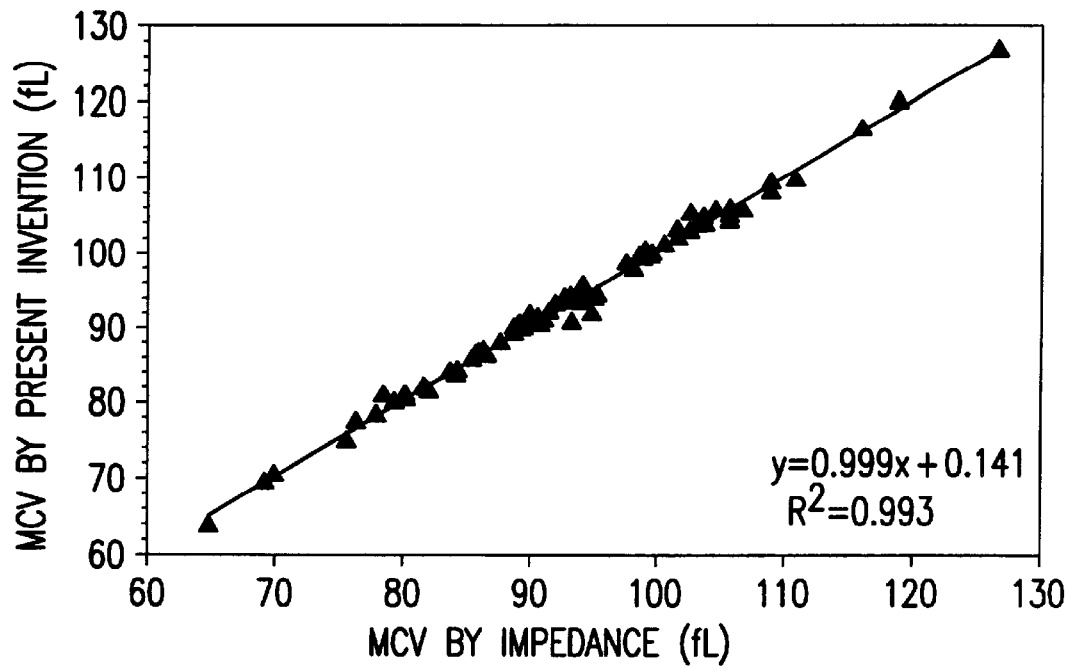
FIG. 8b shows the regression plot of MCV results of the present invention vs. the CELL DYNE® 4000 MCV results (electrical resistivity measurement using hydrodynamically focused impedance aperture) on the same set of normal and clinical samples as in FIG. 8.

Regression statistics and plots of mean cell volume (MCV). FIG. 8a represents the results of the present invention vs. prior art by Tycko (Bayer H*1) and FIG. 8b represent the results of the present invention vs. the CELL DYN® 4000 MCV results (electrical impedance measurement using hydrodynamically-focused cells) on a set of normal and clinical samples.

EXAMPLE 7

Figure 9A:
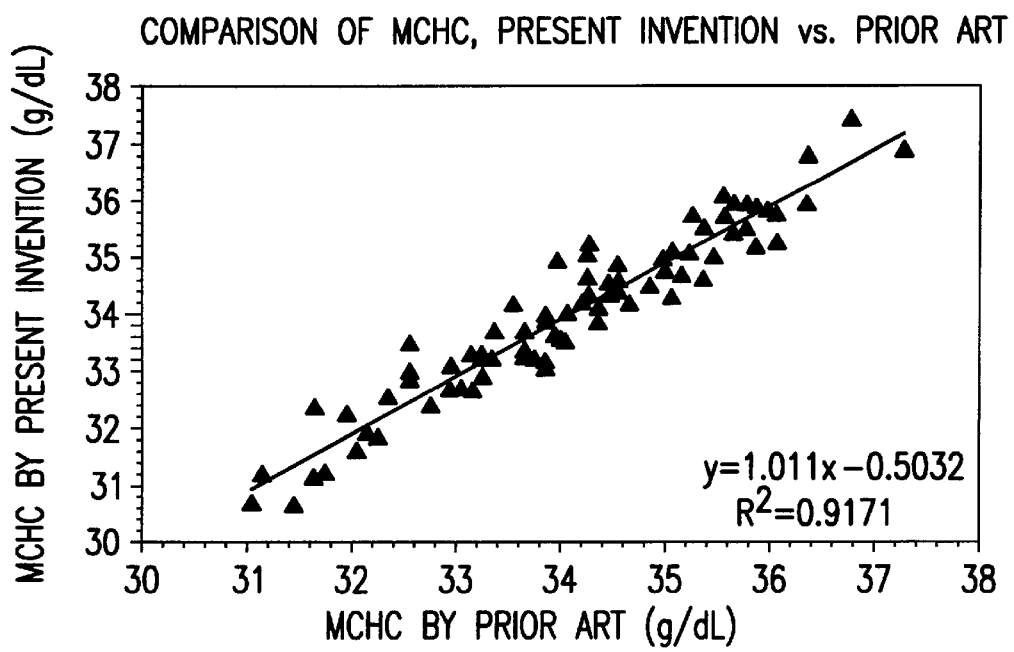
FIG. 9a represents MCHC results of the present invention vs. prior art by Tycko (Bayer H*1 CHCM) on the same set of normal and clinical samples as in FIG. 8.
Figure 9B:
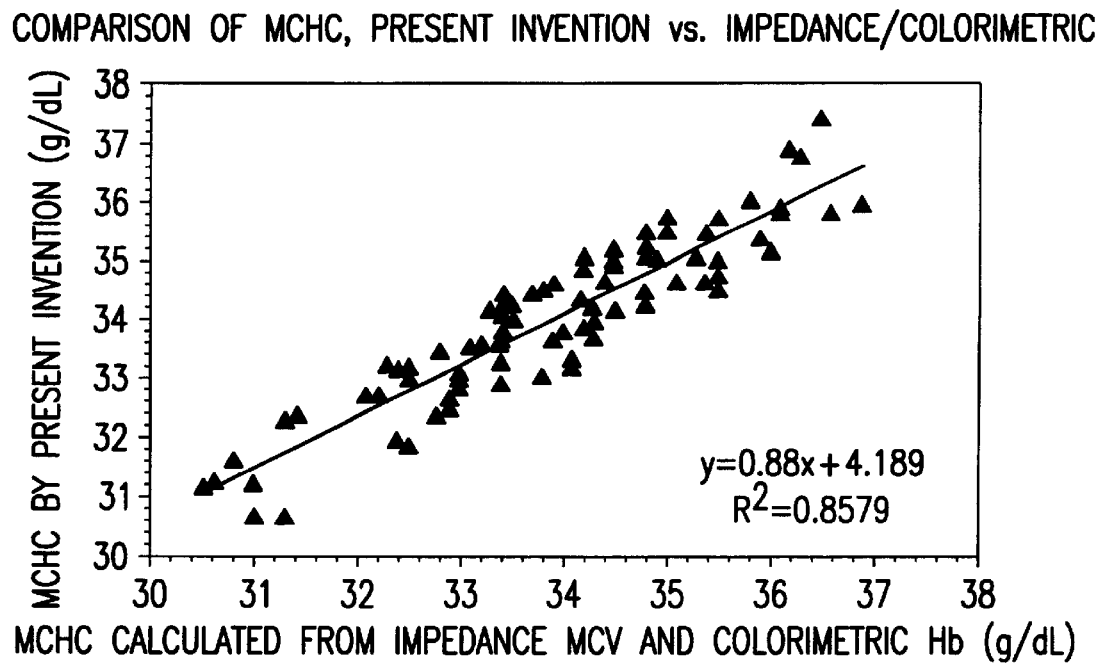
FIG. 9b represents MCHC results of the present invention vs. the CELL DYN™ 4000 MCHC (the results calculated from the impedance MCV and the CELL DYN 4000 colorimetric measurement of hemoglobin) on the same set of normal and clinical samples as in FIG. 8.

Regression statistics of MCHC and the plots. FIG. 9a displays the results of the present invention vs. prior art by Tycko (Bayer H*1 CHCM) and FIG. 9b the results of the present invention vs. the CELL DYN 4000 MCHC (the results calculated from the impedance MCV and the CELL DYN 4000 colorimetric measurement of hemoglobin) on a set of normal and clinical samples.

EXAMPLE 8

Figure 10A:
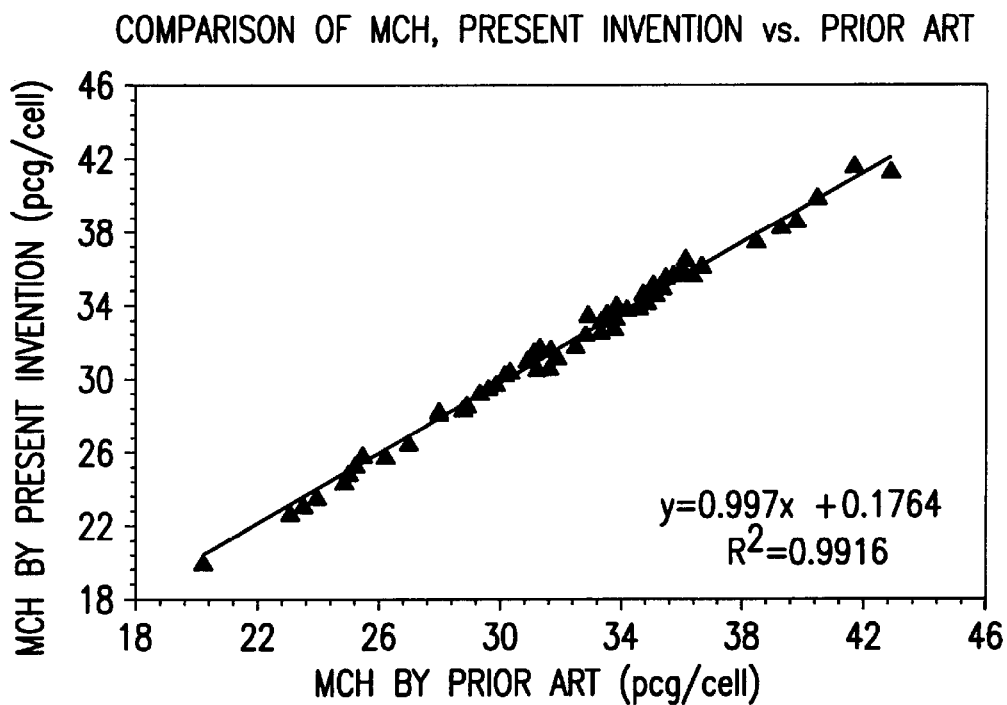
FIG. 10a represents MCH results of the present invention vs. prior art by Tycko (Bayer H*1 MCH) on the same set of normal and clinical samples as in FIG. 8.
Figure 10B:
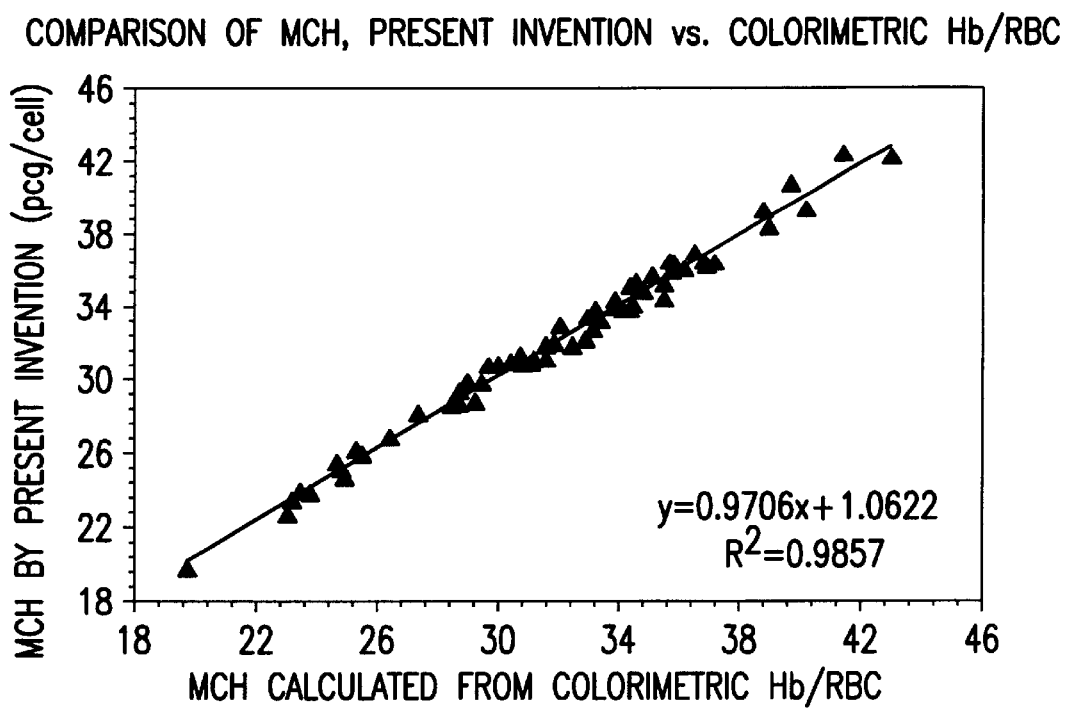
FIG. 10b represents MCH results of the present invention vs. the CELL DYN™ 4000 MCH (calculated from the impedance RBC count and the colorimetric measurement of hemoglobin) on the same set of normal and clinical samples as in FIG. 8.

Regression statistics of MCH and the plots. FIG. 10a is the results of the present invention vs. prior art by Tycko (Bayer H*1 MCH) and FIG. 10b the results of the present invention vs. the CELL DYN 4000 MCH (calculated from the impedance RBC count and the colorimetric measurement of hemoglobin) on a set of normal and clinical samples.

EXAMPLE 9

Figure 11A:
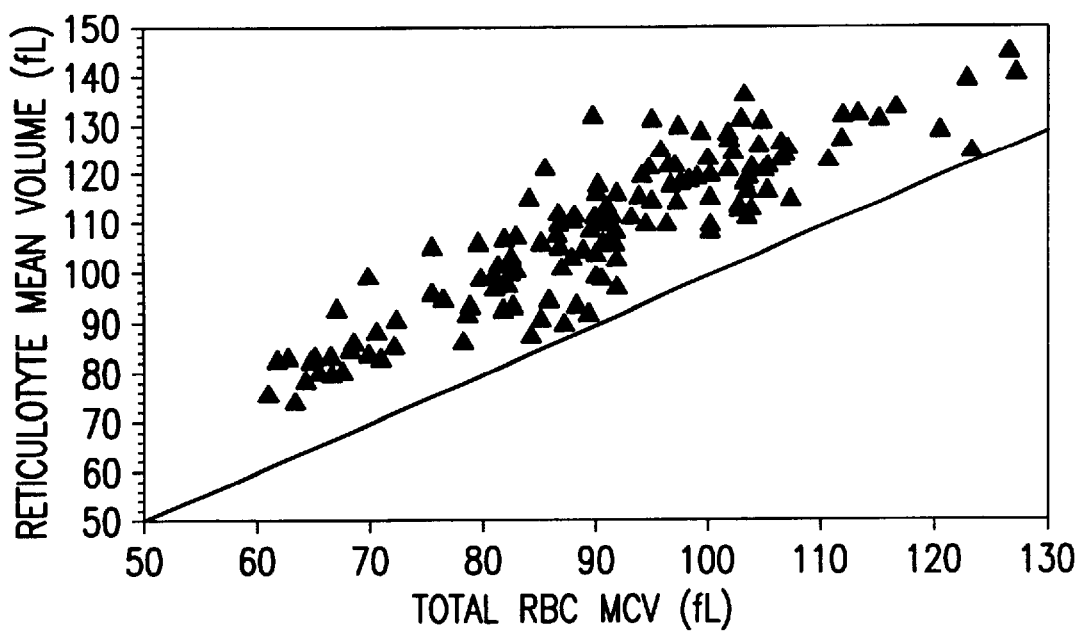
FIG. 11a shows comparison of mean reticulocyte volume (RETV) and total RBC MCV on a set of normal and clinical samples by the method of present invention.
Figure 11B:
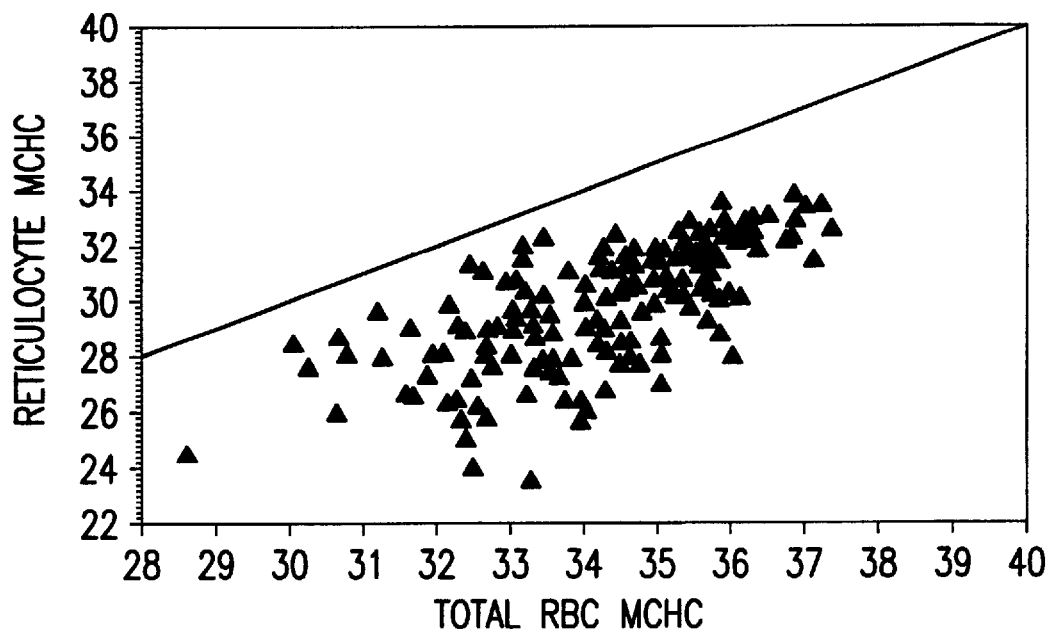
FIG. 11b shows comparison of reticulocyte MCHC (RETHC) and total RBC MCHC on the same set of normal and clinical samples by the method of the present invention.

Comparison of mean reticulocyte volume (RETV) and total RBC MCV on a set of normal and clinical samples by the disclosed method is shown in FIG. 11a and comparison of reticulocyte MCHC (RETHC) and total RBC MCHC on the same set of normal and clinical samples by the disclosed method is shown in FIG. 11b.

EXAMPLE 10

Figure 12A:
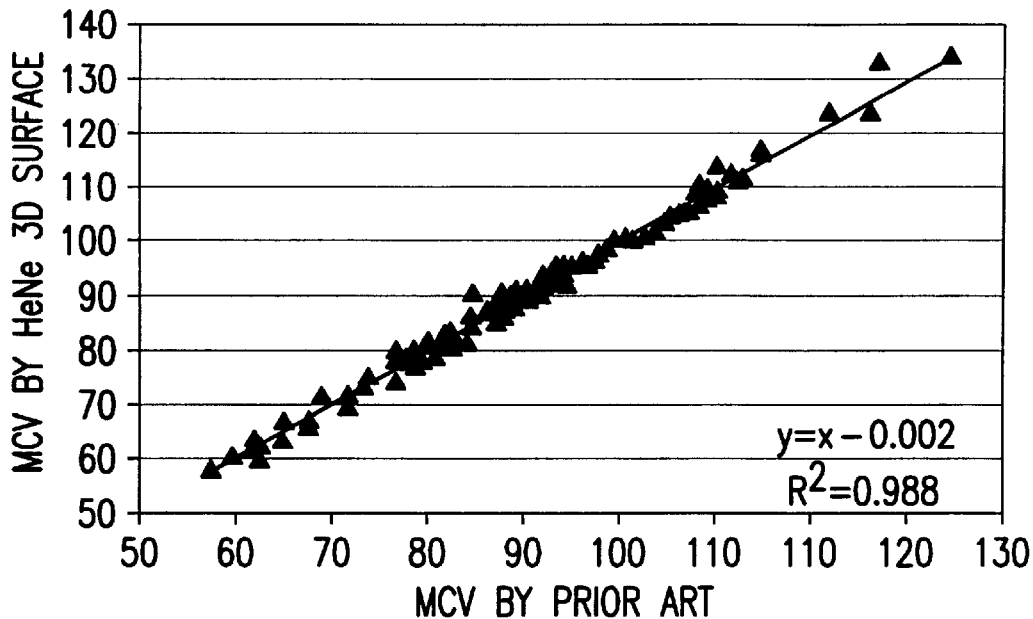
FIG. 12a shows the regression plot of MCV data of the present invention using 633 nm (HeNe laser) light source vs. prior art by Tycko (Bayer H*1) on a set containing 157 normal and clinical samples and 66 osmolarity samples (see Example 10 for detail).
Figure 12B:
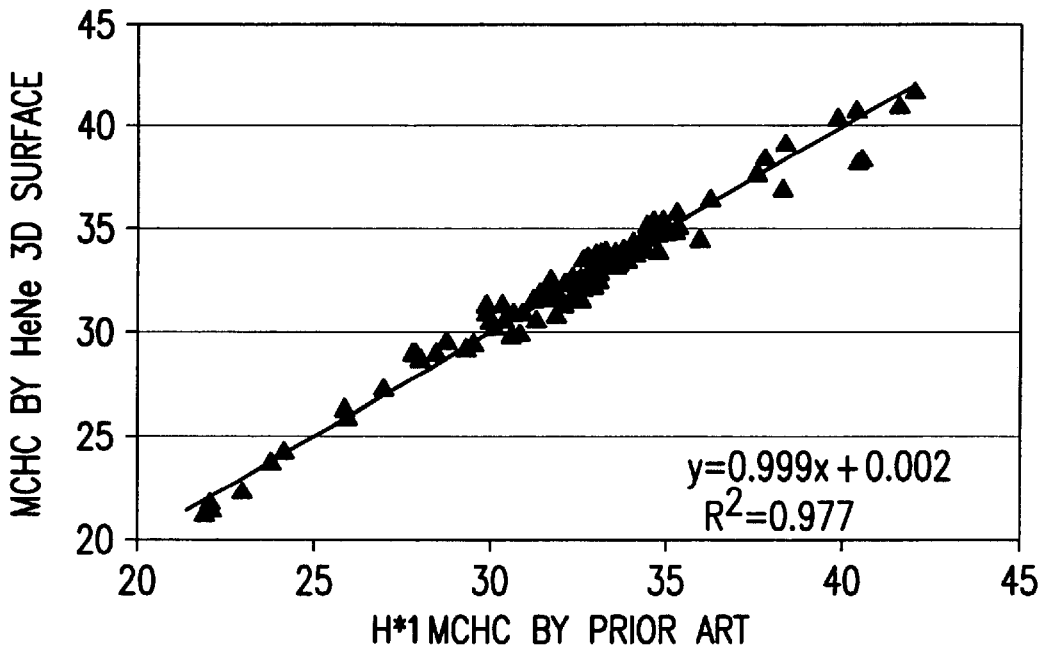
FIG. 12b represents MCHC results of the present invention from the same HeNe system vs. prior art (Bayer H*1 CHCM).

About 1.67 μL of whole blood sample is deposited by means of the sample aspiration probe into the RBC cup, which contains about 2800 µl of the same Diluent used in Example 2 above and mixed. The diluted sample is then transported to the Abbott Cell Dyn 3200 sheathed optical flow cell to collect signals for cell-by-cell volume and hemoglobin measurement. The light source of the Abbott CELL DYN 3200 is 5 mWatt HeNe laser and it's detector is designed to collect two forward light scatter signals at 1°–3° and 3°–10° and 90° +/−30° side scatter signals. The FCS files of the samples are analyzed on the calibrated 3D surface, constructed for the HeNe system, using the disclosed method of the present invention. 157 normal and clinical samples and 66 samples from an osmolarity study were run on the system and the comparison of the results are presented in FIG. 12a and 12b. Osmolarity experiment was conducted by varying the salt concentration of both reagent (CELL DYN 3200 and H*1) used to dilute the blood. Osmolarity range studied was from 175 mOsm/L to 500 mOsm/L.

In view of the above, many advantages of the present invention over the prior art are evident from the foregoing description. While certain representative embodiments and details have been shown for purpose of illustrating the invention, various changes and modifications can be made therein without departing from the scope of the invention defined in the claims.

What is claimed is:

1. A three-dimensional optical method for determining the volume, V, and hemoglobin content, HC, of individual red blood cells, said method comprising the steps of;
   a) treating an anti-coagulated whole blood sample with a reagent solution, said solution comprising a sphering agent and a neutrally buffered isotonic saline solution;
   b) passing a red blood cell isolated from said sample through a light beam directed along an optical path at a selected wave length;
   c) measuring the resultant magnitude of a first forward angle light scatter signal, a second intermediate angle light scatter signal, and a third side-angle light scatter signal from each cell;
   d) projecting a three-dimensional coordinate of said light scatter signals from each cell onto a precalibrated three dimensional surface containing grid lines of V and HC;
   e) determining the values of V and HC by the location of each projected intercept onto said three dimensional grid surface.

2. The method of claim 1, whereby said scatter signals are determined by the volume and hemoglobin concentration of each cell, where said hemoglobin concentration is determined as a function of the index of refraction of hemoglobin at wavelength of said beam of light.

3. The method of claim 1 wherein said selected wavelength corresponds to visible light in a range of 400 nm to 800 nm.

4. The method of claim 1, whereby said three-dimensional surface is calculated based on Mie scatter theory, and is a function of the angles of said three signals relative to the angle of said light beam, the wavelength of said light beam, and the refractive index of hemoglobin at said wavelength.

5. The method of claim 1, whereby said reagent solution further contains a nucleic acid stain which enables separation of reticulocytes from mature red blood cells in said blood sample by means of a fourth fluorescence signal.

6. The method of claim 5, which further includes a red blood cell gate for excluding other cellular particles including white blood cells, platelets, and nucleated red blood cells, said gate established by constructing a two-dimensional cytogram of forward scatter and fluorescence.

7. The method of claim 5, which further includes a red blood cell gate for excluding other cellular particles including white blood cells, platelets, and nucleated red blood cells, said gate established by constructing a two-dimensional cytogram of light loss and fluorescence.

8. The method of claim 5, wherein said three dimensional surface grid method is applied to determine volume and hemoglobin concentration of said reticulocytes.

9. The method of claim 1, which includes the identification of abnormally shaped red blood cells by determining the closest distance of the cell point from said three-dimensional grid surface measured in the direction normal to said grid surface.

10. The method of claim 1, wherein one is able to quantify the percent of macrocytes, microcytes, hypochromic cells, hyperchromic cells, or combinations thereof in said blood sample from the bivariate distribution of individual cell volume and hemoglobin concentration of said sample.

11. The method of claim 1, which includes continuous monitoring of system standardization by determining the degree of symmetry of the cell population distances from the three-dimensional grid surface.

12. A three-dimensional optical method for determining the volume, V, and hemoglobin content, HC, of individual red blood cells, said method comprising the steps of;
   a) treating an anti-coagulated whole blood sample with a reagent solution, said solution comprising a sphering agent and a neutrally buffered isotonic saline solution;
   b) passing a red blood cell isolated from said sample through a light beam directed along an optical path at a selected wavelength;
   c) measuring the resultant magnitude of one forward angle light scatter signal, one light loss signal, and a third side-angle light scatter signal from each cell;
   d) projecting a three-dimensional coordinate of said light scatter signals from each cell onto a pre-calibrated three dimensional surface containing grid lines of V and HC;
   e) determining the values of V and HC by the location of each projected intercept onto said three dimensional grid surface.

13. The method of 1 or 12, wherein said sphering agent is a nonionic surfactant.

14. An apparatus for simultaneously determining white blood cell and red blood cell differentiation comprising:
   a) a means for directing a beam of light along an optical path;
   b) a means for passing a cell through said light beam to produce light scattering patterns of desired angular intervals;
   c) an optical detector with multiple discrete regions, corresponding to predefined angular intervals;
   d) electronic pre-amp means for selectively isolating desired angular intervals for said white blood cell and said red blood cell differential analysis, respectively;
   e) a means for generating, concurrently, signals from each angular interval, corresponding to the intensity of the scattered light within said angular intervals, respectively; and
   f) a means for determining the volume and hemoglobin concentration on cell by cell basis of said red blood cells, and size and complexity of said white blood cells.

15. The apparatus of claim 14, wherein said determining step includes passing a plurality of said red blood cells, one at a time, through said beam of light, such that each of said red blood cells develops at least a $1^{st}$ forward angle light scatter signal, a $2^{nd}$ intermediate angle light scatter signal, and a $3^{rd}$ side angle light scatter signal to determine the volume, hemoglobin concentration, and cell shape abnormality.

16. The apparatus in claim 15, wherein a further determining step includes means for developing a $4^{th}$ concurrent fluorescent signal of said red blood cells for determining maturity of each cell.

17. The apparatus of claim 14, wherein said determining step includes passing a plurality of said red blood cells, one at a time, through said beam of light, such that each of said red blood cells develops at least one light loss signal, a $2^{nd}$ intermediate angle light scatter signal, and a $3^{rd}$ side angle light scatter signal to determine the volume, hemoglobin concentration, and cell shape abnormality.

18. The apparatus of claim 14, wherein the determining step includes passing a plurality of said white blood cells, one at a time, through said beam of light, such that each of said white blood cells develop at least a $1^{st}$ forward angle light scatter signal, a $2^{nd}$ intermediate angle light scatter signal, a $3^{rd}$ side angle polarized light scatter signal, and a $4^{th}$ side angle depolarized light scatter signal to determine the size, cell internal complexity, and granularity of each cell.

19. The apparatus of claim 14, herein the determining step includes passing a plurality of said white blood cells, one at a time, through said beam of light, such that each of said white blood cells develop at least one light loss signal, a $2^{nd}$ intermediate angle light scatter signal, a $3^{rd}$ side angle polarized light scatter signal, and a $4^{th}$ side angle depolarized light scatter signal to determine the size, cell internal complexity, and granularity of each cell.

20. The apparatus of claim 14, wherein said light beam is selected from the visible spectrum in a range of 400 nm to 800 nm.

21. The apparatus of claim 20, wherein said light source is selected from the group consisting of:
   a) an argon-ion gas laser at 488 nm;
   b) a solid state laser at 532 nm; and
   b) a helium-neon gas laser at 632 nm.
   c) a red diode laser
   d) a green diode laser
   e) a blue diode laser.

* * * * *